US010446007B2

(12) United States Patent
Kawazu et al.

(10) Patent No.: US 10,446,007 B2
(45) Date of Patent: Oct. 15, 2019

(54) WATCHING SYSTEM AND MANAGEMENT SERVER

(71) Applicant: Konica Minolta, Inc., Chiyoda-ku, Tokyo (JP)

(72) Inventors: Keiichi Kawazu, Sagamihara (JP); Takashi Okada, Hino (JP); Yuichi Atarashi, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 16/093,348

(22) PCT Filed: Apr. 12, 2017

(86) PCT No.: PCT/JP2017/014924
§ 371 (c)(1),
(2) Date: Oct. 12, 2018

(87) PCT Pub. No.: WO2017/179606
PCT Pub. Date: Oct. 19, 2017

(65) Prior Publication Data
US 2019/0139390 A1 May 9, 2019

(30) Foreign Application Priority Data
Apr. 14, 2016 (JP) .................. 2016-080923

(51) Int. Cl.
G08B 21/04 (2006.01)
A61G 12/00 (2006.01)
(Continued)

(52) U.S. Cl.
CPC .......... *G08B 21/043* (2013.01); *A61G 12/00* (2013.01); *G06F 3/0482* (2013.01);
(Continued)

(58) Field of Classification Search
None
See application file for complete search history.

(56) References Cited

U.S. PATENT DOCUMENTS 8,653,965 B1 * 2/2014 Otto .................... G08B 21/0453
340/539.12
9,642,529 B1 * 5/2017 Siddiqui .............. A61B 5/0008
(Continued)

FOREIGN PATENT DOCUMENTS

JP 2005253025 A 9/2005
JP 2008054986 A 3/2008
WO 2014050680 A1 4/2014

OTHER PUBLICATIONS

Extended European Search Report corresponding to Application No. 17782419.0-1126/3443944 PCT/JP2017014924; dated Mar. 14, 2019.
(Continued)

Primary Examiner — Curtis J King
(74) Attorney, Agent, or Firm — Cantor Colburn LLP

(57) ABSTRACT

Provided are a watching system and a management server which are capable of obtaining necessary information quickly after the recovery while reducing the burden on the careworkers or the like even when a failure occurs in the network system connecting a mobile terminal with a management server.

10 Claims, 13 Drawing Sheets

(51) Int. Cl.
*G06Q 50/22* (2018.01)
*G08B 21/02* (2006.01)
*G08B 25/04* (2006.01)
*H04M 11/04* (2006.01)
*G16H 40/67* (2018.01)
*G16H 40/20* (2018.01)
*G16H 80/00* (2018.01)
*G06F 3/0482* (2013.01)
*G06F 3/0488* (2013.01)

(52) U.S. Cl.
CPC ......... *G06F 3/04883* (2013.01); *G06Q 50/22* (2013.01); *G08B 21/02* (2013.01); *G08B 21/0469* (2013.01); *G08B 21/0476* (2013.01); *G08B 21/0492* (2013.01); *G08B 25/04* (2013.01); *G16H 40/20* (2018.01); *G16H 40/67* (2018.01); *G16H 80/00* (2018.01); *H04M 11/04* (2013.01)

(56) References Cited

U.S. PATENT DOCUMENTS

| | | | | |
|---|---|---|---|---|
| 9,928,712 | B1* | 3/2018 | Clark | G08B 21/02 |
| 2002/0173991 | A1* | 11/2002 | Avitall | G06Q 50/22 |
| | | | | 705/2 |
| 2003/0010345 | A1* | 1/2003 | Koblasz | A61B 5/1115 |
| | | | | 128/845 |
| 2005/0038674 | A1* | 2/2005 | Braig | G06F 19/3418 |
| | | | | 705/2 |
| 2005/0086072 | A1* | 4/2005 | Fox, Jr. | G06Q 50/22 |
| | | | | 705/2 |
| 2006/0020494 | A1* | 1/2006 | Gallo | G06F 19/3456 |
| | | | | 705/3 |
| 2008/0168118 | A1* | 7/2008 | Hickey | G06F 13/385 |
| | | | | 709/201 |
| 2008/0258881 | A1* | 10/2008 | Manson | H04W 4/02 |
| | | | | 340/286.14 |
| 2008/0294490 | A1* | 11/2008 | Nuhaan | G06Q 10/063114 |
| | | | | 705/7.15 |
| 2010/0001838 | A1* | 1/2010 | Miodownik | G06Q 10/06 |
| | | | | 340/10.1 |
| 2010/0191824 | A1* | 7/2010 | Lindsay | G06Q 50/22 |
| | | | | 709/217 |
| 2011/0010087 | A1* | 1/2011 | Wons | G06Q 10/06 |
| | | | | 701/533 |
| 2011/0131589 | A1* | 6/2011 | Beaty | G06F 9/5077 |
| | | | | 719/318 |
| 2012/0120220 | A1* | 5/2012 | Al-Moosawi | H04N 7/183 |
| | | | | 348/77 |
| 2013/0117039 | A1* | 5/2013 | Washburn | G06Q 50/22 |
| | | | | 705/2 |
| 2013/0238350 | A1* | 9/2013 | Baynham | G06Q 10/109 |
| | | | | 705/2 |
| 2014/0039351 | A1* | 2/2014 | Mix | A61B 5/1114 |
| | | | | 600/587 |
| 2014/0155705 | A1 | 6/2014 | Papadopoulos et al. | |
| 2014/0266642 | A1* | 9/2014 | Girardeau | G08B 25/10 |
| | | | | 340/286.07 |
| 2014/0297327 | A1* | 10/2014 | Heil | G06Q 50/22 |
| | | | | 705/3 |
| 2014/0337045 | A1* | 11/2014 | Scrivner | G06F 19/3468 |
| | | | | 705/2 |
| 2014/0340219 | A1* | 11/2014 | Russell | G08B 21/043 |
| | | | | 340/539.12 |
| 2014/0351099 | A1* | 11/2014 | Zhu | G06Q 10/087 |
| | | | | 705/28 |
| 2015/0033295 | A1* | 1/2015 | Huster | G06F 21/44 |
| | | | | 726/4 |
| 2015/0082542 | A1* | 3/2015 | Hayes | A61G 7/018 |
| | | | | 5/600 |
| 2015/0173674 | A1* | 6/2015 | Hayes | A61B 5/681 |
| | | | | 600/301 |
| 2015/0213220 | A1* | 7/2015 | Courville | G16H 50/30 |
| | | | | 705/2 |
| 2015/0221202 | A1* | 8/2015 | Russell | G08B 21/0446 |
| | | | | 340/573.7 |
| 2015/0281810 | A1* | 10/2015 | Babaguchi | G06Q 10/06311 |
| | | | | 340/870.09 |
| 2016/0027289 | A1* | 1/2016 | Hargis | G16H 50/30 |
| | | | | 340/286.07 |
| 2016/0048835 | A1* | 2/2016 | Mutha | G06Q 20/325 |
| | | | | 705/44 |
| 2016/0183864 | A1* | 6/2016 | Kusens | A61B 5/447 |
| | | | | 340/573.1 |
| 2016/0349941 | A1* | 12/2016 | Johnsen | G06F 3/0482 |
| 2017/0004259 | A1* | 1/2017 | Robinson | G16H 40/20 |
| 2017/0004261 | A1* | 1/2017 | Abou-Hawili | G06F 3/04817 |
| 2017/0053078 | A1* | 2/2017 | Lanzel | A61B 5/742 |
| 2017/0213191 | A1* | 7/2017 | Pitcher | G06Q 10/1095 |
| 2018/0301214 | A1* | 10/2018 | Satake | G06Q 50/22 |
| 2018/0311080 | A1* | 11/2018 | Potter | A61B 90/98 |
| 2019/0108908 | A1* | 4/2019 | Faulks | G16H 40/20 |

OTHER PUBLICATIONS

International Search Report corresponding to Application No. PCT/JP2017/014924; dated Jun. 20, 2017.

* cited by examiner

FIG. 5

| NOTIFICATION-SOURCE ADDRESS (ROOM NUMBER) | NOTIFICATION EVENT | NOTIFICATION DESTINATION ADDRESS (CARE STAFF) |
|---|---|---|
| 192.168.10.120 (ROOM RM-1) | OVERTURNING, FALLING | 192.168.10.25(NA)<br>192.168.10.26(NB)<br>192.168.10.27(NC) |
| 192.168.10.121 (ROOM RM-2) | OVERTURNING, FALLING | 192.168.10.25(NA)<br>192.168.10.26(NB)<br>192.168.10.27(NC) |
| 192.168.10.122 (ROOM RM-3) | OVERTURNING, FALLING, WAKING-UP | 192.168.10.30(ND)<br>192.168.10.31(NE)<br>192.168.10.32(NF) |
| 192.168.10.123 (ROOM RM-4) | OVERTURNING, FALLING, WAKING-UP, LEAVING | 192.168.10.30(ND)<br>192.168.10.31(NE)<br>192.168.10.32(NF) |

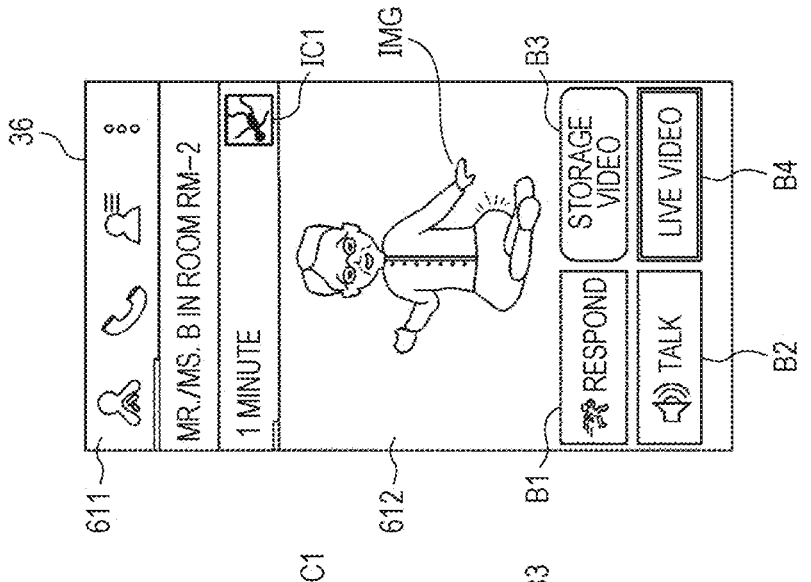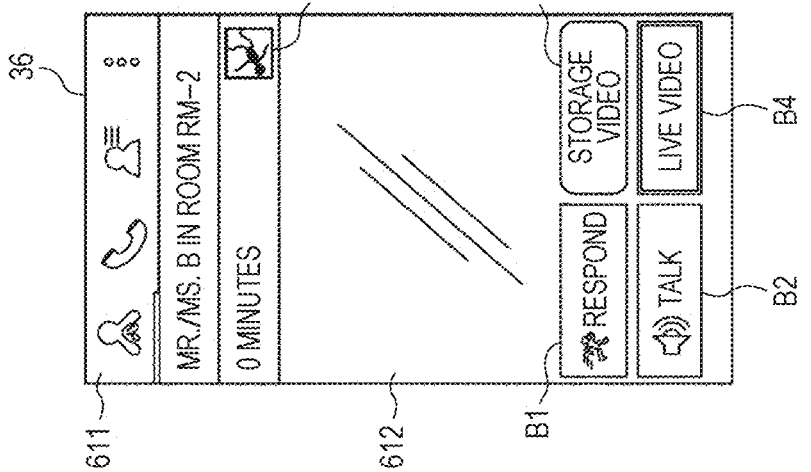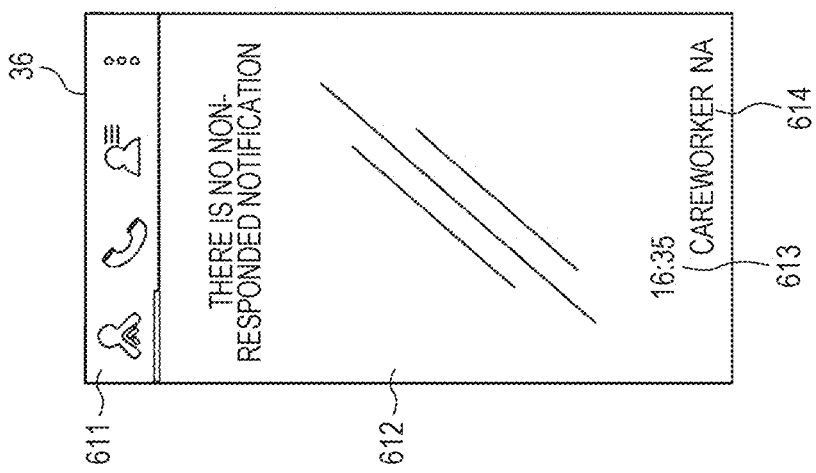

| MOBILE TERMINAL NAME | USER NAME |
|---|---|
| TA-1 | 0001 |
| TA-2 | 0002 |
| TA-3 | 0003 |
| TA-4 | — |
| TA-5 | 0005 |
| TA-6 | — |
| TA-7 | 0010 |

WATCHING SYSTEM AND MANAGEMENT SERVER

CROSS REFERENCE TO RELATED APPLICATIONS

This is the U.S. national stage of application No. PCT/JP2017/014924, filed on Apr. 12, 2017. Priority under 35 U.S.C. § 119(a) and 35 U.S.C. § 365(b) is claimed from Japanese Application No. 2016-080923, filed on Apr. 14, 2016, the disclosures all of which are also incorporated herein by reference.

TECHNICAL FIELD

The present invention relates to a watching system and a management server which are suitably used in nursing care facilities or the like.

BACKGROUND ART

In Japan, the declining birthrate and the aging population are advancing rapidly due to the increase in an average life expectancy of citizens and the decrease in a birthrate. Along with this, hospitals, elderly welfare facilities, and the like that accommodate those who need nursing care (care recipients) are increasing, but a serious situation in which nurses and careworkers are chronically insufficient is caused due to reasons such as a grueling work situation. Particularly, during the night or the like, a small number of people have to watch a lot of care recipients, and thus a burden on careworkers or the like increases, and this is one of causes leading to a further manpower shortage.

In order to alleviate such a burden on the careworkers or the like, a technique for supporting nursing care services is required. For example, various techniques for monitoring the care recipients in order to cause a machine to perform some of works of the careworkers or the like have been developed.

A technique in which, when an abnormality detecting device detects an abnormality in a monitoring target in a facility, images of the monitoring target are captured by a camera installed in a monitoring device, and the image data are transmitted to an external terminal via a network or the like, so that a current state of the monitoring target is remotely monitored is disclosed in Patent Literature 1.

CITATION LIST

Patent Literature

Patent Literature 1: JP 2005-253025 A
Patent Literature 2: JP 2008-54986 A

SUMMARY OF INVENTION

Technical Problem

By using the monitoring device of Patent Literature 1, the care recipients are monitoring targets, and thus unmanned monitoring can be performed, so that the burden on the careworkers or the like is reduced. Here, in a case in which the careworkers or the like are informed of the abnormality in the care recipient, it is also possible to display an alarm on a fixed terminal installed in a nurse station or the like. However, during the night or the like, the careworkers or the like are not necessarily in the nurse station, and they may go out to look around, and in this case, the careworkers or the like may not notice the abnormality in the care recipient in time. On the other hand, if information indicating that the abnormality in the care recipient occurs is transmitted to mobile terminals carried by the careworkers or the like at all times, and the alarm is displayed on the basis of the information, for example, the careworkers or the like can be expected to take a prompt action even while looking around. On the other hand, since information of the care recipient is related to privacy, it is not appropriate to make it accessible by everyone. In this regard, when the mobile terminal is used, it is preferable that necessary information can be obtained after transmitting login information to a management server and obtaining login authentication. If the careworkers or the like can access the information of the care recipient, it is possible to give an appropriate care in time.

By the way, although a network system connecting the mobile terminal with the management server generally uses commercial electric power, temporary power outage may occur due to, for example, natural disasters or accidents. If the power outage occurs, the mobile terminal and the management server are unable to communicate with each other, and the mobile terminal is unable to access the management server, and thus necessary information is unable to be accessed. On the other hand, when recovered from the power outage, if the user logs in again, the mobile terminal can again access the management server, but since one care recipient is often watched by a plurality of careworkers, it is difficult for individual careworkers or the like to immediately determine what extent an action has been taken for the target person for whom the careworker is responsible before communication is disconnected, and thus there is a possibility of confusion of nursing care. For such a problem, if a large capacity backup power supply capable of maintaining the network system for a certain period of time is installed, an unexpected situation such as the power outage can be dealt with, but the cost will be greatly increased.

On the other hand, a slot machine that performs a power interruption process of restoring to a control state before power interruption at the time of restoration from the power interruption when the power interruption is detected is disclosed in Patent Literature 2. By diverting this related art, it is possible to restore the network system connecting the mobile terminal with the management server to the state before the power outage, but there is a problem in that the system is complicated and expensive, interference between software or the like is likely to occur, and an error is likely to occur. Further, even though the network system is restored to the state before the power outage, what to deal with it is still unclear to the careworkers or the like at the present time, and a better system is desired.

The present invention was made in light of the foregoing, and it is an object of the present invention to provide a watching system and a management server which are capable of obtaining necessary information quickly after the recovery while reducing the burden on the careworkers or the like even when a failure occurs in the network system connecting the mobile terminal with the management server.

Solution to Problem

In order to achieve at least one of the above objects, a watching system in which one aspect of the present invention is reflected includes:

a sensor device that receives data from a watching target person and outputs a signal corresponding to the data;

a management server that is communicably connected to the sensor device via a network; and a mobile terminal that is capable of performing wireless communication with the management server via the network and outputs a watching alarm on the basis of a signal transmitted from the sensor device via the management server, wherein, when the mobile terminal transmits login information to the management server via the network, the management server permits the mobile terminal to log in, so that information related to the watching target person stored in the management server is accessible from the mobile terminal, and the management server causes transition from unprocessed information to processed information to be performed in a case in which there is a response indicating responding in the information related to the watching target person accessed from the mobile terminal, when the mobile terminal transmits logout information to the management server, the management server permits the mobile terminal to log out, so that the information related to the watching target person stored in the management server is inaccessible from the mobile terminal, and in a case in which the mobile terminal that has logged in is unable to perform communication with the management server, the management server stores the unprocessed information before the communication is unable to be performed, and then when the mobile terminal is able to perform communication with the management server, the management server transmits a notification indicating that the unprocessed information is stored to the mobile terminal, and the mobile terminal presents information indicating that the unprocessed information is stored to the management server in response to the notification.

In order to achieve at least one of the above objects, a management server in which one aspect of the present invention is reflected includes:

a communication unit that performs communication with a sensor device that receives data from a watching target person and outputs a signal corresponding to the data, and a mobile terminal that outputs a watching alarm on the basis of a signal transmitted from the sensor device, via a network; and a storage that stores various kinds of information, in which, when login information transmitted by the mobile terminal via the network is received by the communication unit, the mobile terminal is permitted to log in, so that information related to the watching target person stored in the storage is accessible from the mobile terminal, transition from unprocessed information to processed information is performed in a case in which there is a response indicating responding in the information related to the watching target person accessed from the mobile terminal, when logout information transmitted from the mobile terminal is received by the communication unit, the mobile terminal is permitted to log out, so that the information related to the watching target person stored in the storage is inaccessible from the mobile terminal, and in a case in which the mobile terminal that has logged in is unable to perform communication with the management server, the unprocessed information before the communication is unable to be performed is stored in the storage, and then when the mobile terminal is able to perform communication with the management server, a notification indicating that the unprocessed information is stored in the storage is transmitted from the communication unit to the mobile terminal, and the mobile terminal is able to present information indicating that the unprocessed information is stored in the storage in response to the notification.

Advantageous Effects of Invention

According to the present invention, it is possible to provide a watching system and a management server which are capable of obtaining necessary information quickly after the recovery while reducing the burden on the careworkers or the like even when a failure occurs in the network system connecting the mobile terminal with the management server.

BRIEF DESCRIPTION OF DRAWINGS

FIG. 5 is a diagram illustrating a configuration of a transmission destination information table in a watching system of the present embodiment.

FIG. 7A to FIG. 7C are diagrams illustrating an example of a display screen of a mobile terminal of the present embodiment.

DESCRIPTION OF EMBODIMENTS

Figure 1:
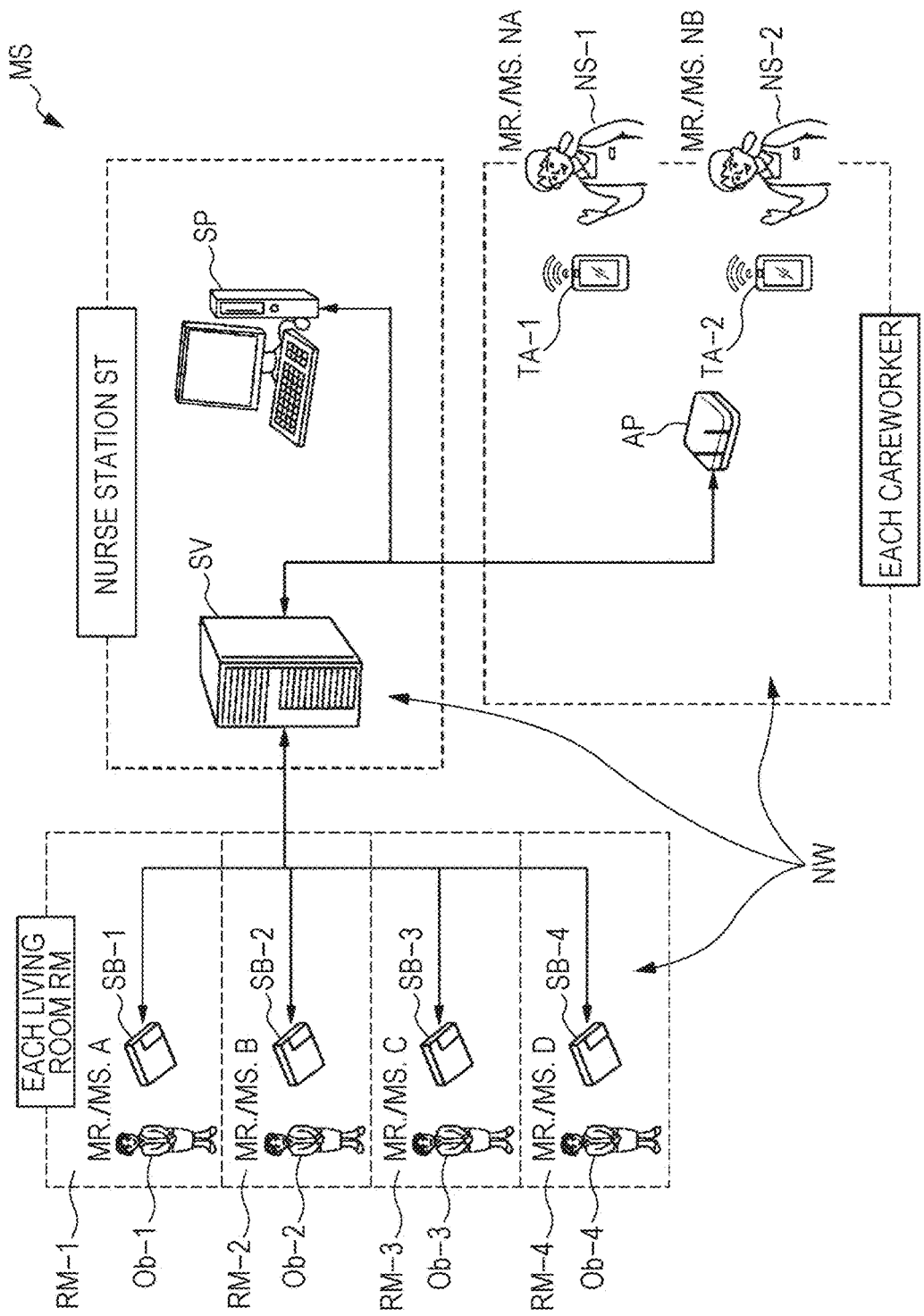
FIG. 1 is a diagram illustrating an overall configuration of a watching system in the present embodiment.
Figure 2:
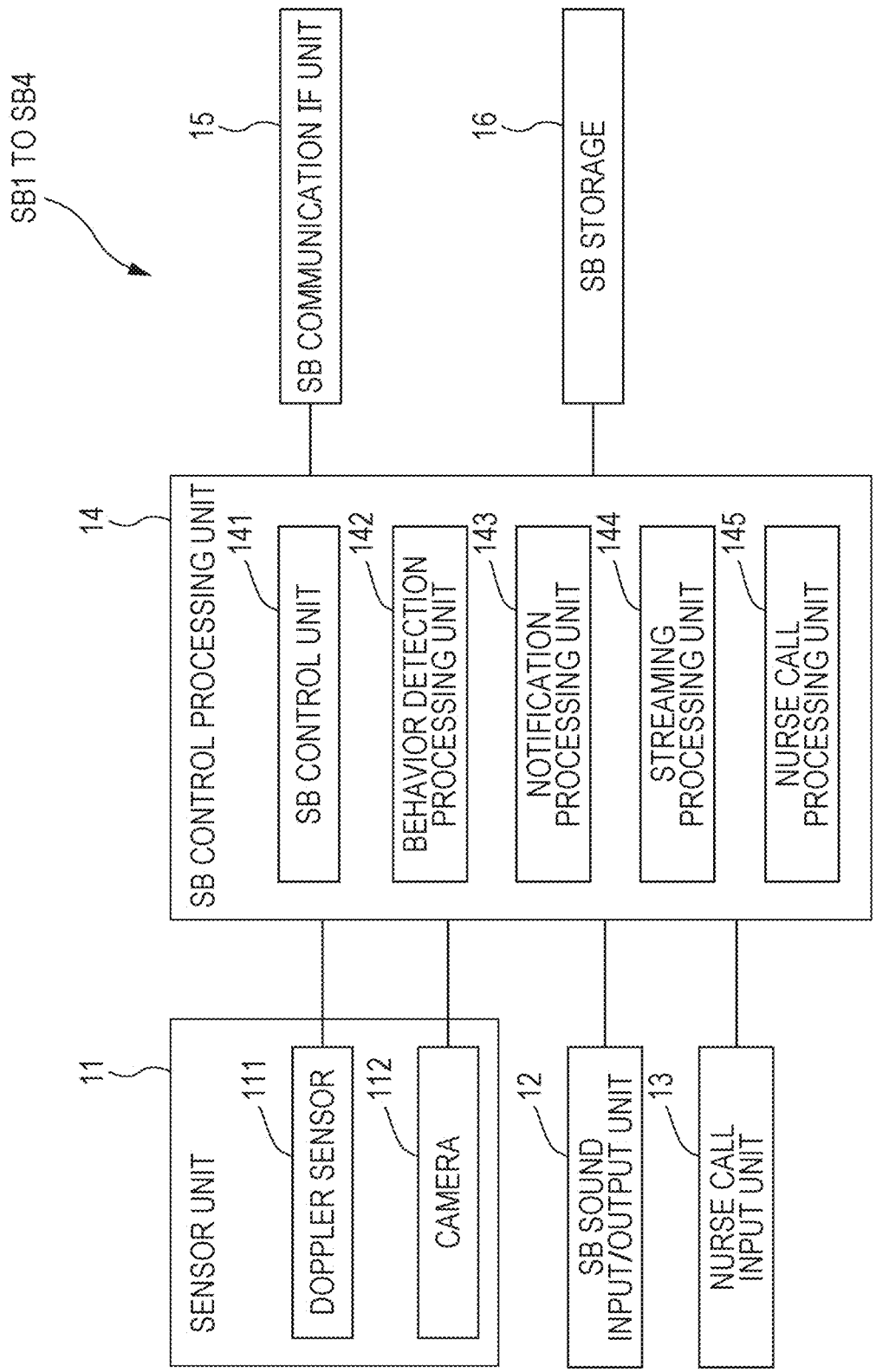
FIG. 2 is a diagram illustrating a configuration of a sensor box in a watching system of the present embodiment.
Figure 3:
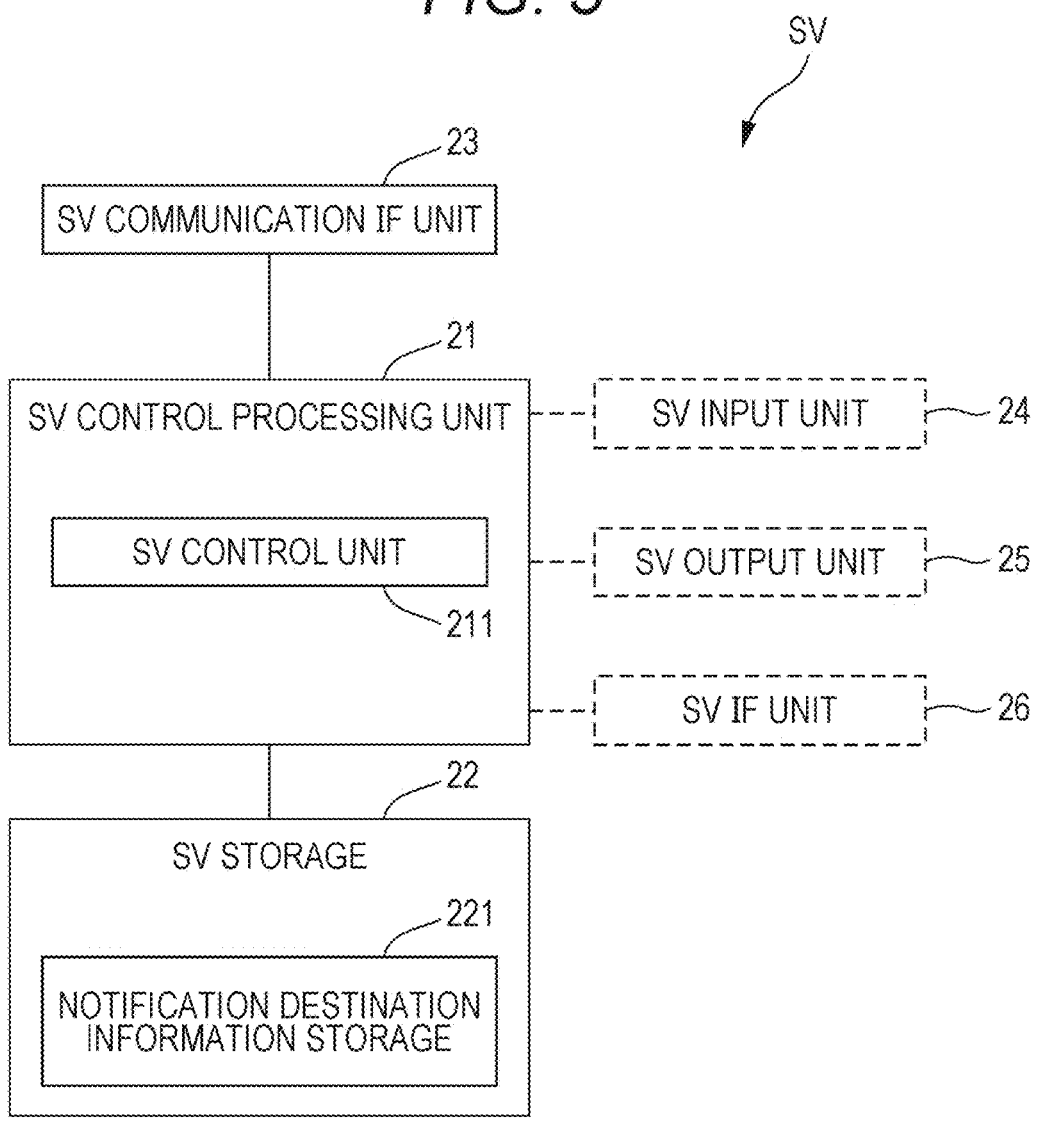
FIG. 3 is a diagram illustrating a configuration of a management server in a watching system of the present embodiment.
Figure 4:
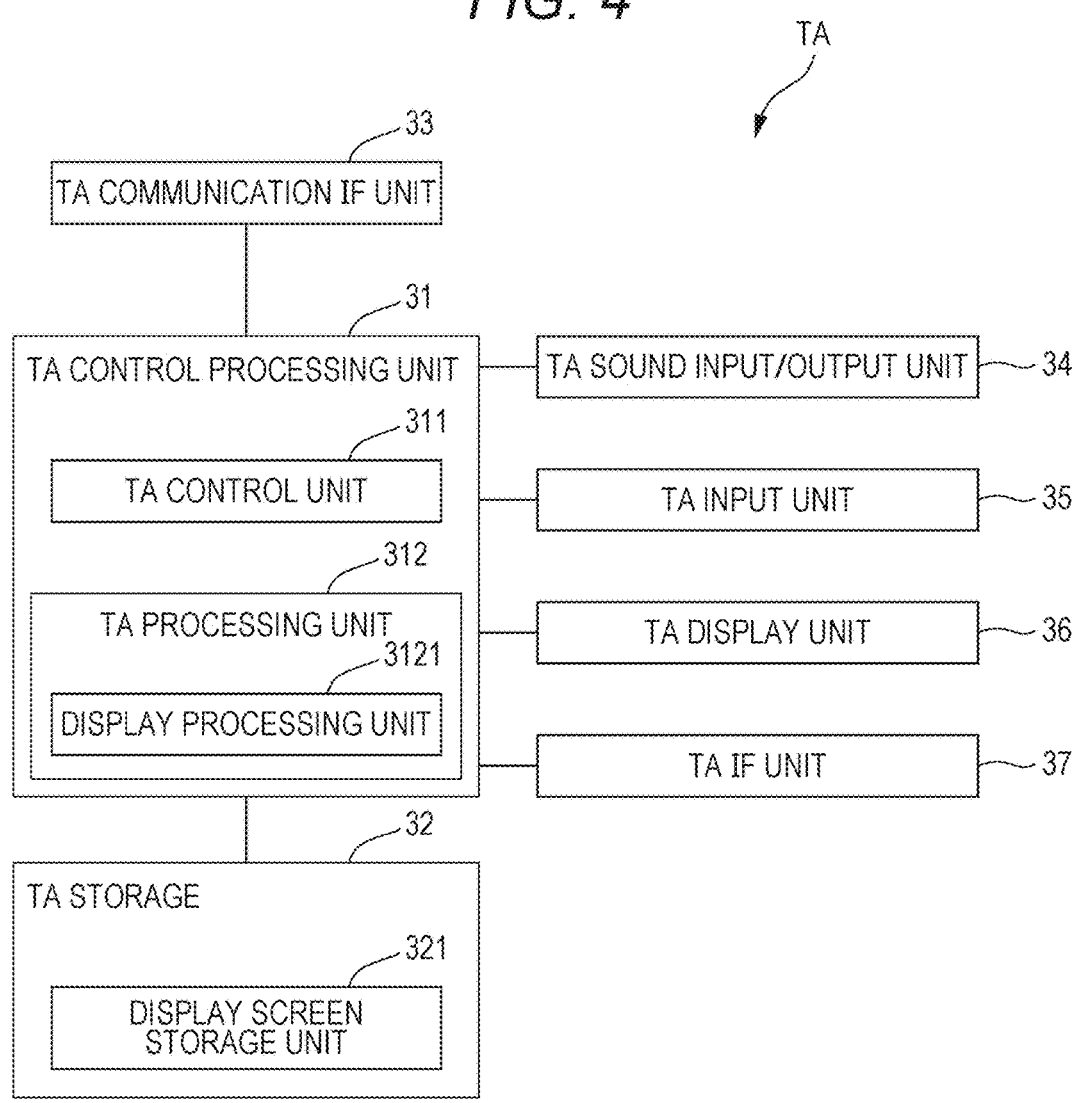
FIG. 4 is a diagram illustrating a configuration of a mobile terminal in a watching system of the present embodiment.

Hereinafter, the present invention will be described with reference to the appended drawings. FIG. 1 is a diagram illustrating an overall configuration of a watching system in the present embodiment. FIG. 2 is a diagram illustrating a configuration of a sensor box in a watching system of the present embodiment. FIG. 3 is a diagram illustrating a configuration of a management server in a watching system of the present embodiment. FIG. 4 is a diagram illustrating a configuration of a mobile terminal in a watching system of the present embodiment. FIG. 5 is a diagram illustrating a configuration of a transmission destination information table in a watching system of the present embodiment. In this specification, "nursing care" is a concept including "nursing".

The watching system in the present embodiment has a function of detecting a state of a monitored person (hereinafter referred to as a target person) Ob who is a watching target through each corresponding sensor box SB, watching the target person Ob, and supporting nursing.

For example, as illustrated in FIG. 1, such a watching system MS includes sensor boxes SB (SB-1 to SB-4) which are installed in living rooms of the target persons, a management server SV, a fixed terminal device SP, and mobile terminals TA (TA-1 and TA-2) managed by the careworkers, which are communicably connected via a network (a network or a communication line) NW such as a local area network (LAN), a telephone network, or a data communication network in a wired or wireless manner. A repeater which relays communication signals such as a repeater, a bridge, a router, or a cross-connect may be installed in the network NW. In the example illustrated in FIG. 1, a plurality of sensor boxes SB-1 to SB-4, the management server SV, the fixed terminal device SP, and a plurality of mobile terminals TA-1 and TA-2 are communicably connected with one another via a wireless LAN NW including an access point AP (for example, a LAN according to an IEEE 802.11 standard, or the like). The sensor box SB corresponds to an example of a sensor device, and each of the fixed terminal device SP and the mobile terminal TA corresponds to an example of a terminal.

The target person Ob is, for example, a person who needs nursing due to sickness or injury, a person who needs nursing care due to a decline in physical ability or the like, a solitary person living alone, or the like. In particular, from the viewpoint of enabling early detection and early treatment, the target person Ob is preferably a person who needs to be discovered when a predetermined unfavorable event such as an abnormal state occurs in the person. For this reason, the watching system MS is suitably installed in buildings such as hospitals, aged welfare facilities, and dwellings depending on a type of target person Ob. In the example illustrated in FIG. 1, the watching system MS is installed in a building of a nursing facility including a plurality of living rooms RM which a plurality of target persons Ob occupy and a plurality of rooms such as the nurse stations ST.

First, the sensor box SB will be described. The sensor box SB is arranged on each of a ceiling, a wall, or the like of the living room RM of the target person Ob and has a communication function of communicating with the management server SV or the like via the network NW. More specifically, as illustrated in FIG. 2, the sensor box SB includes a sensor unit 11, an SB sound input/output unit 12, a nurse call input unit 13, an SB control processing unit 14, an SB communication IF unit 15, and an SB storage 16.

The sensor unit 11 is connected to the SB control processing unit 14, detects the state of the target person Ob under the control of the SB control processing unit 14, and outputs corresponding state data. In the present embodiment, the states of the target person Ob include waking-up, leaving bed, overturning, falling, and a subtle body movement abnormality of the target person Ob, and in order to detect these states, the sensor unit 11 includes, for example, a Doppler sensor 111 and a camera 112.

The Doppler sensor 111 is a body movement sensor that transmits a transmission wave, receives a reflection wave of the transmission wave reflected by the object, and outputs a Doppler signal of a Doppler frequency component on the basis of the transmission wave and the reflection wave. In a case in which the object is moving, a frequency of the reflection wave is shifted in proportion to a moving speed of the object due to the so-called Doppler effect, and thus a difference (a Doppler frequency component) occurs between the frequency of the transmission wave and the frequency of the reflection wave. The Doppler sensor 111 generates a signal of the Doppler frequency component as a Doppler signal and outputs the Doppler signal to the SB control processing unit 14. The transmission wave may be an ultrasonic wave, a microwave, or the like, but in the present embodiment, the transmission wave is a microwave. Since the microwave can pass through clothes and be reflected against the body surface of the target person Ob, it is possible to detect the motion of the body surface even in a state in which the target person Ob is wearing clothes, and thus the microwave is preferable.

The camera 112 is connected to the SB control processing unit 14 and is a device that generates an image (image data) under the control of the SB control processing unit 14. The camera 112 is arranged to be able to monitor a space (the space in the living room RM in the example illustrated in FIG. 1) in which the target person Ob to be monitored is supposed to be located, images the space as an imaging target from above, generates an image (image data) in which the imaging target is overlooked, and outputs the image of the imaging target to the SB control processing unit 14. Preferably, since a probability that the entire target person Ob can be imaged is high, the camera 112 is installed to be able to image the imaging target directly above a preset supposed head position (usually, a position at which a pillow is placed) at which the head of the target person Ob is supposed to be located on a bedding (for example, a bed or the like) on which the target person Ob is lying. The sensor box SB acquires the image of the target person Ob captured above the target person Ob, preferably, an image captured directly above the supposed head position through the camera 112 of the sensor unit 11.

The camera 112 may be a device that generates an image of visible light, but in the present embodiment, the camera has a function of generating an image of infrared rays so that the target person Ob can be monitored even in a relatively dark place. For example, in the present embodiment, the camera 112 is a digital infrared camera including an imaging optical system that forms an infrared optical image in an imaging target on a predetermined imaging plane, an image sensor that is arranged so that a light receiving surface matches the imaging plane and converts an infrared optical image in the imaging target into an electric signal, an image processing unit that performs image processing on an output of the image sensor and generates image data which is data indicating an infrared image in the imaging target, and the like. In the present embodiment, it is preferable that the imaging optical system of the camera 112 be a wide-angle optical system (so-called wide angle lens (including a fisheye lens)) having an angle of field at which the entire living room RM of the target person Ob can be imaged. Further, an infrared illumination device that illuminates the space with infrared rays may be further installed.

The SB sound input/output unit 12 is a circuit that is connected to the SB control processing unit 14 and acquires an external sound and inputs the external sound to the sensor box SB and generates and outputs a sound corresponding to an electrical signal indicating a sound in accordance with the control of the SB control processing unit 14. The SB sound input/output unit 12 includes, for example, a microphone or the like that converts an acoustic vibration of a sound into an electrical signal, and a speaker or the like that converts an electrical signal of a sound into an acoustic vibration of a sound. The SB sound input/output unit 12 outputs an electrical signal indicating an external sound to the SB control processing unit 14, and converts an electrical signal input from the SB control processing unit 14 into an acoustic vibration of a sound and outputs the acoustic vibration of the sound. Further, preferably, the SB sound input/output unit 12 is detachable from the sensor box SB main body and is connected to the SB control processing unit 14 in a wired or wireless manner and placed at an arbitrary position in the living room. Further, in a case in which the SB sound input/output unit 12 is wirelessly connected to the SB control processing unit 14, it is preferable to install a device that monitors the battery level in the SB sound input/output unit 12 and informs a manipulator or the like of the battery level. Alternatively, in a case in which the SB sound input/output unit 12 is connected to the SB control processing unit 14 in a wired manner, it is preferable to install a device that informs the manipulator or the like of whether or not an appropriate connection is established.

The nurse call input unit 13 is a push button type switch or the like connected to the SB control processing unit 14. In a case in which a resident desires to make a nurse call, if an input manipulation is received by the nurse call input unit 13, an electrical signal indicating that a nurse call is received is output from the nurse call input unit 13 to the SB control processing unit 14, and a signal is transmitted to the mobile terminal TA of the careworker or the like accordingly. At this time, it is preferable that signal transmission being in progress be indicated, for example, by turning on a lamp attached to the nurse call input unit 13.

The SB communication IF unit 15 is a communication circuit that is connected to the SB control processing unit 14 and performs communications under the control of the SB control processing unit 14. The SB communication IF unit 15 generates a communication signal containing data to be transferred which is input from the SB control processing unit 14 in accordance with a communication protocol used in the network NW of the watching system MS and transmits the generated communication signal to the management server SV or the like via the network NW. Further, the SB communication IF unit 15 receives a communication signal from the management server SV or the like via the network NW, extracts data from the received communication signal, converts the extracted data into a data of a format processible by the SB control processing unit 14, and outputs the converted data to the SB control processing unit 14. Incidentally, the SB communication IF unit 15 may further include an interface circuit that performs input and output of data with an external device using a standard such as a mobile phone communication network, a WiFi standard, Bluetooth (registered trademark) standard, an infrared data association (IrDA) standard, or a universal serial bus (USB) standard.

The SB storage 16 is a circuit that is connected to the SB control processing unit 14 and stores various kinds of programs and various kinds of data under the control of the SB control processing unit 14. Examples of various kinds of programs include a control process program such as a monitoring process program that executes information processing related to monitoring of the target person Ob. The monitoring process program includes a notification process program that gives a notification to the outside in a case in which a predetermined event (event) occurs, a processing program that delivers an image (moving image) captured by the camera 112 to the fixed terminal device SP or the mobile terminal TA which has requested the image, a nurse call process program that performs a voice call with the fixed terminal device SP or the mobile terminal TA using the SB sound input/output unit 12 or the like. The various kinds of data include data necessary for executing each program, data necessary for monitoring the target person Ob, and the like in addition to data of a moving image captured by the camera 112 and state data such as subtle body movement data acquired by the Doppler sensor 111. The SB storage 16 includes, for example, a read only memory (ROM) which is a non-volatile memory element, an electrically erasable programmable read only memory (EEPROM) which is a rewritable non-volatile memory element, and the like. Further, the SB storage 16 includes a random access memory (RAM) or the like serving as a so-called working memory of the SB control processing unit 14 that stores data and the like generated while the program is being executed.

The SB control processing unit 14 is a circuit that receives a nurse call, generates a moving image, and detects a preset predetermined behavior in the target person Ob. The SB control processing unit 14 includes, for example, a central processing unit (CPU) and peripheral circuits thereof. The SB control processing unit 14 functionally includes a sensor control unit (SB control unit) 141, a behavior detection processing unit 142, a notification processing unit 143, a streaming processing unit 144, and a nurse call processing unit 145 as the control process program is executed.

The SB control unit 141 controls the sensor box SB in general.

The behavior detection processing unit 142 detects preset predetermined events in the target person Ob on the basis of an output of the sensor unit 11. In the present embodiment, as described above, the predetermined events include waking-up, leaving bed, overturning, falling, and the subtle body movement abnormality of the target person Ob, and the behavior detection processing unit 142 detects waking-up, leaving bed, overturning, falling, and the subtle body movement abnormality of the target person Ob as events on the basis of the output of the sensor unit 11 and notifies the notification processing unit 143 of the detection events. The behavior detection processing unit 142 can distinguish and detect waking-up, leaving bed, overturning, falling, and the subtle body movement abnormality of the target person Ob on the basis of the output of the sensor unit 11. For example, the behavior detection processing unit 142 extracts a moving body region from the image acquired by the camera 112 of the sensor unit 11 as a human body region of the target person Ob, determines a posture of the target person Ob (for example, standing, sitting, lying, or the like) from an aspect ratio of the extracted moving body region, detects the position of the detected moving body region, and determines a distinction of the waking-up, leaving bed, overturning, and falling on the basis of these judgments, the posture and the position of the detected target person Ob. Further, in a case in which transition from the lying posture to the sitting posture in the bed region is detected, the behavior detection processing unit 142 determines that it is waking-up and determines that an event of waking-up (a waking-up event) occurs. Further, in a case in which transition from the sitting posture in the bed region to the standing posture outside the bed region is detected, the behavior detection processing unit 142 determines that it is leaving bed and determines that an event of leaving bed (a leaving bed event) occurs. Further, in a case in which transition from the inside of the bed region to the outside of the bed region is detected, and then the lying posture outside the bed region is detected, the behavior detection processing unit 142 determines that it is falling and determines that an event of falling (a falling event) occurs. Further, for example, in a case in which transition from the sitting posture or the standing posture to the lying posture outside the bed region is detected, for example, the behavior detection processing unit 142 determines that it is overturning and determines that an event of overturning (an overturning event) occurs. Further, the behavior detection processing unit 142 detects the body movement of the chest portion (a vertical movement of the chest portion) associated with a breathing motion of the target person Ob by the Doppler sensor 111 of the sensor unit 11, and if disturbance in a cycle in the body movement of the chest portion or an amplitude in the body movement of the chest portion which is equal to or less than a preset threshold value is detected, the behavior detection processing unit 142 determines that it is the subtle body movement abnormality and determines that an event of a subtle body movement abnormality (a subtle body movement abnormality event) occurs. The behavior detection processing unit 142 has a function of performing determination on the basis of a stored routine behavior of the target person, and when a behavior different from the stored normal behavior occurs or when a behavior corresponding to stored dementia or the like occurs, the behavior detection processing unit 142 determines that an abnormality event occurs and give a notification to the mobile terminal TA as will described later. Here, it is preferable that determination criteria (determination algorithms) of the behavior detection processing unit 142 in all the sensor boxes SB be identical to one another. Accordingly, the determination criteria need not be changed even if the resident changes, and it does not take time and efforts. Here, the determination criteria of the behavior detection processing unit 142 may be customized for each sensor box SB.

In a case in which the input manipulation is received by the nurse call input unit 13, the nurse call processing unit 145 gives a notification indicating an event, more specifically, the manipulation of the nurse call (nurse call event) to the notification processing unit 143. Then, the nurse call processing unit 145 can perform voice communication with the fixed terminal device SP or the mobile terminal TA via the network NW through the SB communication IF unit 15.

The notification processing unit 143 gives a notification to the outside in a case in which the nurse call event by the nurse call input unit 13 and a predetermined event in which a predetermined behavior in the target person Ob is detected by the sensor unit 11 (in the present embodiment, respective events of waking-up, leaving bed, overturning, and falling) occur in the sensor box SB. More specifically, the notification processing unit 143 generates a notification signal including information indicating a type of occurred event (in the present embodiment, information identifying the nurse call event or a predetermined detection event (waking-up, leaving bed, overturning, falling, and the subtle body movement abnormality, that is, information indicating a type obtained by classifying a predetermined state) and identifier information specifying and identifying the sensor box SB detecting the target person Ob, and transmits the notification signal from the SB communication IF unit 15 to the management server SV via the network NW. Alternatively, if there is a request (a state data request signal is transmitted) from the outside, the notification processing unit 143 generates a communication signal containing state data such as image data and transmits the communication signal from the SB communication IF unit 15 to the management server SV via the network NW.

Further, although not used in an operation of a ladder chart to be described later, in a case in which there is a request to deliver a streaming moving image from the fixed terminal device SP or the mobile terminal TA via the network NW through the SB communication IF unit 15, the streaming processing unit 144 delivers a moving image (for example, a live moving image) generated by the camera 112 of the sensor unit 11 to the fixed terminal device SP or the mobile terminal TA which has made the request via the network NW through the SB communication IF unit 15 in a streaming reproduction manner.

FIG. 1 illustrates four sensor boxes, that is, first to fourth sensor boxes SB-1 to SB-4 as an example, and the first sensor box SB-1 is installed in a living room RM-1 of Mr./Ms. A Ob-1 who is one of the target persons Ob, the second sensor box SB-2 is installed in a living room RM-2 of Mr./Ms. B Ob-2 who is one of the target persons Ob, the third sensor box SB-3 is installed in a living room RM-3 of Mr./Ms. C Ob-3 who is one of the target persons Ob, and the fourth sensor box SB-4 is installed in a living room RM-4 of Mr./Ms. D Ob-4 who is one of the target persons Ob.

In the sensor box SB, if its operation starts, the sensor unit 11 outputs an image generated by imaging a living space from above at a predetermined frame rate and a Doppler signal to the SB control processing unit 14. The behavior detection processing unit 142 of the SB control processing unit 14 detects the presence or absence of a predetermined behavior in the target person Ob on the basis of the image and the Doppler signal at predetermined time intervals, and if the predetermined behavior is detected as a detection event, the behavior detection processing unit 142 of the SB control processing unit 14 gives a notification indicating the detection event and a type of detection event to the notification processing unit 143. Upon receiving the notification indicating the detection event, the notification processing unit 143 transmits a notification signal from the SB communication IF unit 15 to the management server SV.

Further, although not used in the operation of the ladder chart to be described later, if the input manipulation is received by the nurse call input unit 13, the nurse call processing unit 145 gives a notification indicating the nurse call reception event to the notification processing unit 143. Upon receiving the notification indicating the reception event, the notification processing unit 143 transmits a notification signal from the SB communication IF unit 15 to the management server SV. The management server SV gives a notification indicating that the nurse call occurs to the mobile terminal TA carried by the careworker who is responsible for the living room in which the nurse call occurs.

Next, the management server SV will be described. In FIG. 1, the management server SV has a communication function of independently communicating with the other sensor boxes SB, the fixed terminal device SP, and the mobile terminal TA via the network NW. The management server SV has a function of receiving a notification from the sensor box SB and providing information to the mobile terminal TA carried by the careworker who is responsible for the living room in which the event occurs and/or the fixed terminal device SP. As illustrated in FIG. 3, for example, the management server SV includes an SV control processing unit 21, an SV storage 22, and an SV communication IF unit 23.

Similarly to the SB communication IF unit 15, the SV communication IF unit 23 is a communication device which is connected to the SV control processing unit 21 and performs communication under the control of the SV control processing unit 21. The SV communication IF unit 23 generates a communication signal containing data to be transferred which is input from the SV control processing unit 21 in accordance with a communication protocol used in the network NW of the watching system MS and transmits the generated communication signal to the sensor box SB or the like via the network NW The SV communication IF unit 23 receives the communication signal from the sensor box SB or the like via the network NW, extracts data from the received communication signal, converts the extracted data into data of a format processible by the SV control processing unit 21, and outputs the converted data to the SV control processing unit 21.

The SV storage 22 is a circuit which is connected to the SV control processing unit 21 and stores various kinds of programs and kinds of various data under the control of the SV control processing unit 21. Examples of the various programs include a control process program such as a server program or the like that provides the client with data corresponding to a request of a client (in the present embodiment, the fixed terminal device SP, the mobile terminal TA, or the like). The various kinds of data include data necessary for executing each program, data necessary for monitoring the target person Ob such as monitoring information related to monitoring of the target person Ob, notification destination information related to a notification destination of the event, and the like. Similarly to the SB storage 16, the SV storage 22 includes, for example, a ROM, an EEPROM, and the like. The SV storage 22 includes a RAM or the like serving as a so-called working memory of the SV control processing unit 21 that stores data or the like generated while the predetermined program is being executed.

The SV storage 22 includes a notification destination information storage 221 that stores the notification destination information. The notification destination information storage 221 stores the notification destination information related to the notification destination of the event. The notification destination information is information indicating a notification destination to which a notification of the event contained in the received notification signal is given in a case in which the notification signal is received from the sensor box SB. For example, in the present embodiment, the notification destination information is information indicating a correspondence relation between the sensor box SB of the transmission source that transmits the notification signal and the mobile terminal TA that transmits the notification signal received from the sensor box SB, and is stored in, for example, the notification destination information storage 221 in a table format as illustrated in FIG. 5. A notification destination information table 41 illustrated in FIG. 5 includes a notification source address field 411 in which a communication address of the sensor box SB serving as the transmission source of the notification signal is registered, a notification event field 412 in which notification event information is given in a case in which the target person is in this state, and a notification destination address field 413 in which a communication address of the mobile terminal TA that gives a notification of an event contained in the notification signal received from the sensor box SB having the communication address associated with the communication address of the sensor box SB registered in the notification source address field 411 is registered and has a record for each sensor box SB. Incidentally, the communication address of the sensor box SB may be used as the identifying information ID, and the notification source address field 411 need not be necessarily installed, but in a case in which the notification source address field 411 is installed, the number of a room in which the sensor box SB is installed may be registered. Further, the communication address of the mobile terminal TA may be terminal identifier information (terminal ID) specifying and identifying the mobile terminal TA, and for example, a name of an observer such as a name of the careworker carrying the mobile terminal TA may be registered in the notification destination address field 413. An item of the notification event (notification event information) in the notification event field 412 can be set from the management server SV side in accordance with the target person Ob in the living room in which the sensor box SB is installed. In the example of FIG. 5, it means that in the case of Mr./Ms. A and Mr./Ms. B, a notification is given in a case in which an event of overturning or falling occurs, and in the case of Mr./Ms. C, a notification is given in a case in which an event of overturning, falling, or waking-up occurs, and in the case of Mr./Ms. D, a notification is given in a case in which an event of overturning, falling, waking-up, or leaving bed occurs. For example, it is preferable to classify the notification event in accordance with the target person due to reasons such as the state of the target person (what there are a person for whom no response is determined to be necessary since there is hardly any problem after waking-up and a person for whom a response is determined to be necessary), previous response information (what there is a person for whom no response is determined to be necessary in first leaving bed since the person has a habit of repeating leaving bed and getting into bed a few times in the past), and the like.

The SV control processing unit 21 is a circuit which receives the notification from the sensor box SB and transfers the received notification to the fixed terminal device SP and the corresponding mobile terminal TA. The SV control processing unit 21 includes, for example, a central processing unit (CPU) and peripheral circuits thereof.

The SV control unit 211 of the SV control processing unit 21 controls the management server SV in general.

Incidentally, as indicated by broken lines in FIG. 3, the management server SV may further include a server input unit (SV input unit) 24 which is connected to the SV control processing unit 21 and receives various kinds of commands and various kinds of data if necessary, a server output unit (SV output unit) 25 that outputs various kinds of commands and various kinds of data received by the SV input unit 24, information related to monitoring of the target person Ob, and the like, a server interface unit (SV IF unit) 26 that performs input and output of data with an external device, and the like. The management server SV can be constituted by, for example, a computer with a communication function.

The fixed terminal device SP is a device which is installed in the nurse station ST, has a communication function of communicating with the management server SV or the like via the network NW, a display function of displaying predetermined information, an input function of receiving a predetermined instruction or data, and the like, and functions as a user interface (UI) of the watching system MS by receiving a predetermined instruction or data input to the management server SV or the mobile terminal TA and displaying a detection result or an image obtained by sensor box SB. The fixed terminal device SP can be constituted by, for example, a computer with a communication function. It is preferable that the fixed terminal device SP can detect the state in the living room through the function of the sensor box SB in all the living rooms in which the sensor box SB is installed.

Next, the mobile terminal TA will be described. The mobile terminal TA is a device which has a communication function of communicating with the management server SV or the like via the network NW, a display function of displaying predetermined information, an input function of receiving a predetermined instruction or data, a call function of making a voice call, and the like and receives a predetermined instruction or data input to the management server SV or the sensor box SB, receives a notification of a predetermined event in a case in which the predetermined event occurs in the sensor box SB, makes a call with the sensor box SB, and displays a moving image generated by the sensor box SB.

In the present embodiment, the mobile terminal TA includes, for example, a TA control processing unit 31, a TA storage 32, a TA communication IF unit 33, a TA sound input/output unit 34, a TA input unit 35, a TA display unit 36, and a TA IF unit 37 as illustrated in FIG. 4.

The TA sound input/output unit 34 is a device which is connected to the TA control processing unit 31 and acquires an external sound and inputs the acquired sound to the mobile terminal TA, and generates and outputs a sound corresponding to an electrical signal indicating a sound in accordance with the control of the TA control processing unit 31. Similarly to the SB sound input/output unit 12, the TA sound input/output unit 34 includes, for example, a microphone or the like that converts an acoustic vibration into an electrical signal, and a speaker or the like that converts an electrical signal of a sound into an acoustic vibration of a sound. The TA sound input/output unit 34 outputs an electrical signal indicating the external sound to the TA control processing unit 31, converts the electrical signal input from the TA control processing unit 31 into an acoustic vibration of the sound and outputs the acoustic vibration of the sound.

The TA input unit 35 is a device which is connected to the TA control processing unit 31 and receives, for example, a predetermined manipulation and inputs the predetermined manipulation to the mobile terminal TA and includes a plurality of input switches or the like to which predetermined functions are allocated. Examples of the predetermined manipulation include various kinds of manipulations necessary for monitoring such as an input manipulation of an ID for logging-in, a response manipulation corresponding to the nurse call a notification of which is given, a request manipulation for a moving image, an input manipulation indicating that there is an intention to execute a response such as lifesaving, nursing, nursing care, or assistance on the target person Ob a notification of which is given (restoration). The TA display unit 36 serving as an information presenting unit is a device which is connected to the TA control processing unit 31 and displays predetermined manipulation content input from the TA input unit 35 and the monitoring information related to monitoring of the target person Ob monitored by the watching system MS (for example, an event that occurs in the sensor box SB, an image of the target person Ob, or the like) under the control of the TA control processing unit 31 and includes, for example, a display device such as an LCD or an organic EL display. Then, in the present embodiment, the TA input unit 35 and the TA display unit 36 are configured with a touch panel. In this case, the TA input unit 35 is a position input device that detects and receives a manipulation position such as a resistive type or a capacitive type. In the touch panel, the position input device is installed on the display surface of the TA display unit 36, and candidates of one or more pieces of input content which can be input to the TA display unit 36 are displayed, and for example, if the user (observer) such as the careworker touches a display position at which input content desired to be input is displayed, the position is detected by the position input device, and display content displayed at the detected position is input to the mobile terminal TA as the manipulation input content of the user.

The TA IF unit 37 is a device which is connected to the TA control processing unit 31 and performs input and output of data with an external device under the control of the TA control processing unit 31, and includes, for example, an interface circuit using a mobile phone communication network, a WiFi standard, or Bluetooth (registered trademark), an interface circuit that performs infrared communication of an IrDA standard or the like, an interface circuit using a USB standard, or the like.

Similarly to the SB communication IF unit 15, the TA communication IF unit 33 is a communication device which is connected to the TA control processing unit 31 and performs communication under the control of the TA control processing unit 31. The TA communication IF unit 33 generates a communication signal containing data to be transferred which is input from the TA control processing unit 31 in accordance with a communication protocol used in the network NW of the watching system MS and transmits the generated communication signal to the management server SV or the like via the network NW. The TA communication IF unit 33 receives the communication signal from the management server SV or the like via the network NW, extracts data from the received communication signal, converts the extracted data into data of a format processible by the TA control processing unit 31 and outputs the converted data to the TA control processing unit 31.

Similarly to the SB storage 16, the TA storage 32 is a circuit which is connected to the TA control processing unit 31 and stores various kinds of programs and various kinds of data under the control of the TA control processing unit 31. The various kinds of programs include a display process program for processing an operation related to display and the like. The various kinds of data include each piece of data such as screen information displayed on the TA display unit 36. The TA storage 32 includes, for example, a ROM, an EEPROM, and the like. The TA storage 32 includes a RAM or the like serving as a so-called working memory of the TA control processing unit 31 that stores data and the like generated while the predetermined program is being executed. The TA storage 32 functionally includes a display screen storage 321 in order to store the above-described respective pieces of information.

The display screen storage 321 stores the screen information to be displayed on the TA display unit 36 under control of a display processing unit 3121 to be described later in the TA control processing unit 31.

The TA control processing unit 31 is a circuit for processing information. Similarly to the SB control processing unit 14, the TA control processing unit 31 includes, for example, a CPU and peripheral circuits thereof. The TA control processing unit 31 functionally includes a TA control unit 311 and a TA processing unit 312 as a control process program is executed, and the TA processing unit 312 functionally includes the display processing unit 3121.

The TA control unit 311 controls the mobile terminal TA in general.

The display processing unit 3121 processes an operation related to the display of the TA display unit 36. More specifically, the display processing unit 3121 displays the moving image on the TA display unit 36 if necessary.

The mobile terminal TA can be constituted by a portable communication terminal device such as a so-called tablet type computer, a smart phone, a cellular phone, or the like.

Figure 6:
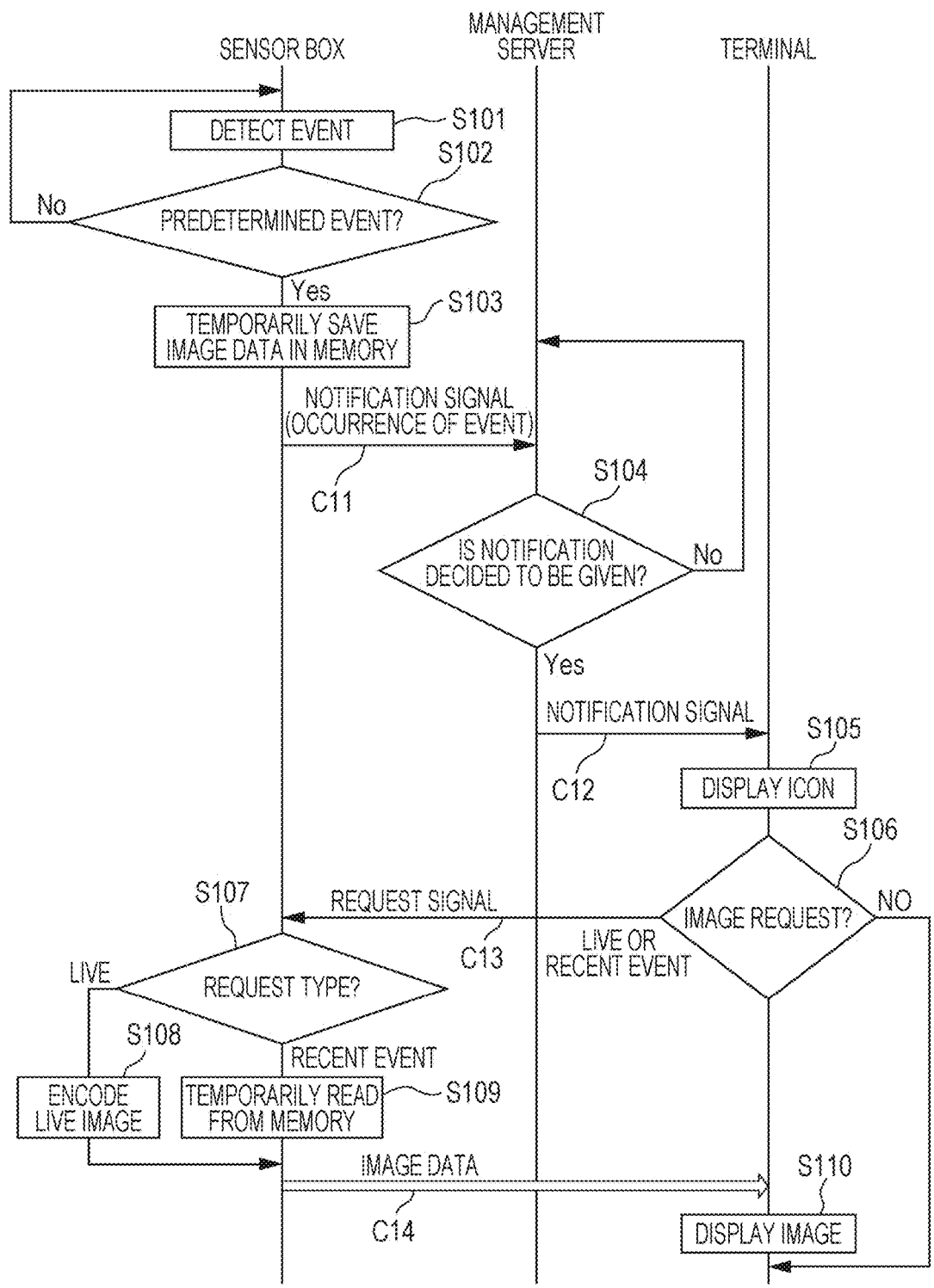
FIG. 6 is a ladder chart diagram illustrating an operation of a watching system of the present embodiment.

Next, an operation of the watching system in the embodiment will be described. FIG. 6 is a ladder chart diagram illustrating the operation of the watching system of the present embodiment. FIG. 7A to FIG. 7C are diagrams illustrating an example of the display screen of the mobile terminal of the present embodiment.

In the watching system MS having the above configuration, if activated, as the control process program is executed in the sensor box SB, the SB control unit 141, the behavior detection processing unit 142, the notification processing unit 143, the streaming processing unit 144, and the nurse call processing unit 145 are functionally configured in the SB control processing unit 14, and as the control process program is executed in the management server SV, the SV control unit 211 is functionally configured in the SV control processing unit 21. Further, as the control process program is executed in the mobile terminal TA, the TA processing unit 312 functionally including the TA control unit 311 and the display processing unit 3121 is functionally configured in the TA control processing unit 31.

The operation of the watching system MS will be described, but description of the nurse call event will be omitted. In the mobile terminal TA, upon accepting a login manipulation (to be described later in detail) of, for example, the careworker, the mobile terminal TA displays a standby screen in which it is on standby for a communication signal destined for the mobile terminal TA on the TA display unit 36 through the TA processing unit 312. For example, as illustrated in FIG. 7A, the standby screen has a menu bar region 611 in which a menu bar is displayed and a standby main region 612 in which a message indicating that it is on standby (for example, "there is no non-responded notification"), a date or a current time, and a user name (careworker) logged in the mobile terminal TA, and the like are displayed. If the standby screen is displayed, the mobile terminal TA is on standby for the communication signal in the TA communication IF unit 33 by the TA control unit 311.

In step S101 of FIG. 6, the sensor box SB samples output data of the Doppler sensor 111 of the sensor unit 11 at a sampling period corresponding to a predetermined frame rate through the SB control unit 141, acquires image data through the camera 112, stores the image data in a ring buffer (not illustrated), and analyzes the sampled and acquired output data of the Doppler sensor 111 and the image data of the camera 112 through the behavior detection processing unit 142. In a case in which the SB control unit 141 does not detect a predetermined event (waking-up, leaving bed, overturning, falling, and the subtle body movement abnormality) in step S102 as a result of the analysis, the flow returns to step S101, and the detection operation is continued. On the other hand, when the SB control unit 141 detects a predetermined event, in step S103, the image data and/or the subtle body movement data before and after the event are extracted from the ring buffer and stored in the SB storage 16. Here, it is possible to cause the detection operation of the sensor box SB to be interrupted only in, for example, a time zone set through the fixed terminal device SP. It is also possible to change the program in the sensor box SB, for example, through the fixed terminal device SP.

Further, the sensor box SB transmits a notification signal including event information indicating a type of occurred notification event and a communication address to the management server SV via the network NW through the notification processing unit 143 (C11). Since the notification signal does not include the image data of the target person, an amount of information is small.

If the notification signal is transmitted from the sensor box SB, in step S104, the management server SV collates information included in the notification signal from the notification destination information table 41 stored in the notification destination information storage 221, and determines who the resident (here, Mr./Ms. B) is from the communication address of the transmission destination corresponding to the communication address of the transmission source, and further determines whether or not it corresponds to the type of notification event (here, overturning or falling) corresponding to the resident (Mr./Ms. B) from the event information of the notification signal. Then, in a case in which the event information of the received notification signal indicates the notification event, the notification is decided to be given to the terminal. On the other hand, in a case in which the event information of the received notification signal does not indicate the notification event (waking-up or leaving bed in case of Mr./Ms. B), the notification is decided not to be given to the terminal, and it is on standby for a next notification signal.

If the notification is decided to be given to the terminal, the management server SV performs collation in the notification destination information table 41 stored in the notification destination information storage 221 and selects the mobile terminal TA of the transmission destination from the communication address of the transmission destination corresponding to the communication address of the transmission source. More specifically, in the notification destination information table 41 stored in the notification destination information storage 221, the communication address of the notification destination registered in the notification destination address field 413 in the record in which the communication address of the transmission source of the received notification signal is registered is registered in the notification source address field 411 is extracted. For example, in a case in which the notification signal from the sensor box SB-2 having a communication address "192.168.10.121" installed in the room RM-2 is received, three communication addresses "192.168.10.25", "192.168.10.26", and "192.168.10.27" of the notification destinations registered in the notification destination address field 413 in a record of a second line in which the communication address "192.168.10.121" of the transmission source of the notification signal is registered are extracted. Incidentally, in this example, the communication address "192.168.10.25" is a communication address assigned to the mobile terminal TA-1 carried by a careworker NA, the communication address "192.168.10.26" is a communication address assigned to the mobile terminal TA-2 carried by a careworker NB, and the communication address "192.168.10.27" is a communication address assigned to the mobile terminal TA-3 carried by a careworker NC (not illustrated).

Then, the management server SV transmits a notification signal (an event signal, that is, a watching alarm) including information in which overturning or falling occurs in the room RM-2 to the selected mobile terminals TA-1 to TA-3 and the fixed terminal device SP(C12).

In a case in which the notification signal is transmitted from the management server SV, the mobile terminal TA switches the screen display of the TA display unit 36 to, for example, that illustrated in FIG. 7B by the TA processing unit 312. At this time, a sound or a voice (for example, a voice message such as "falling occurs in the room RM-2") may be output through the TA sound input/output unit 34 serving as the presenting unit, or a notification indicating that the notification signal is received may be given to the careworker through vibration or the like.

In the example illustrated in FIG. 7B, a name of the living room in which the event occurs (the room RM-2, that is, information related to the sensor box which has transmitted the notification), a name of the resident of the living room (Mr./Ms. B), an icon IC1 indicating overturning or falling (that is, information indicating that an event signal (notification) is received), and a time difference (0 minutes) between a notification time and the present are displayed in the main region 612 (step S105). At the same time, buttons B1 (respond), B2 (talk), B3 (watch storage video), and B4 (watch live video) are displayed in the main region 612.

Here, if the careworker touches the button B3 or B4, the TA input unit 35 of the mobile terminal TA reacts, and in step S106, the TA control unit 311 determines that an image request is made and transmits a request signal (a state data request signal) from the TA communication IF unit to the management server SV via the network NW (C13). Here, the request signal includes a request type (a storage video or a live video). The management server SV relays the request signal to be transmitted to the target sensor box SB. Here, the request signal may be transmitted directly to the sensor box SB.

Upon receiving the request signal, the sensor box SB determines the request type in the request signal in step S107. If the careworker touches the button B3, since a request signal for requesting the storage image is output from the mobile terminal TA, it is determined that the sensor box SB which has received the request signal via the management server SV is requesting the storage video, and in step S109, the image data is read out from the SB storage 16 and transmitted from the SB communication IF unit 15 to the management server SV via the network NW (C14). Alternatively, if the careworker touches the button B4, since a request signal for requesting the live video is output from the mobile terminal TA, it is determined that the sensor box SB which has received the request signal via the management server SV is requesting the live video, in step S108, the live video captured by the camera 112 is encoded and transmitted from the SB communication IF unit 15 to the management server SV via the network NW (C14). The live video may be extracted from the ring buffer. The management server SV relays the image data to be transmitted to the mobile terminal TA which has transmitted the request signal. Further, the image data may be directly transmitted to the mobile terminal TA.

Upon receiving the image data, the mobile terminal TA switches the screen display of the TA display unit 36 to, for example, that illustrated in FIG. 7C by the TA processing unit 312. In the example illustrated in FIG. 7C in which the storage video is requested, images (video) IMG of Mr./Ms. B before and after overturning in the room RM-2 is displayed in the main region 612, and the careworker who viewed the image IMG can determine whether or not it is a state which should be responded immediately. Alternatively, in a case in which determination is unable to be performed by just looking at the image IMG, the careworker can touch the button B2 and then talk directly with Mr./Ms. B through the SB sound input/output unit 12 of the sensor box SB, and thus the careworker can accurately determine the situation. Alternatively, in a case in which the live video is requested, the image displayed on the mobile terminal TA is a current streaming image. In the above example, the notification signal is transmitted to the mobile terminal TA, but the notification signal may be transmitted to the mobile terminal TA and/or to the fixed terminal device SP. Here, the image request can be arbitrarily performed regardless of the notification signal.

Further, when the careworker who viewed the icon IC1 displayed in step S105 is near the room RM-2 in which the event occurred, the careworker may rush immediately without looking at the image. Accordingly, in this case, if the button B1 is touched, information indicating that the careworker directly responds is transmitted to the fixed terminal device SP. If the button B1 is touched, preferably, the display corresponding to the notification signal is canceled in the other mobile terminals TA and/or the fixed terminal device SPto which the notification signal has been transmitted, and the display returns to the display of FIG. 7A, or display indicating "careworker in charge is responding" is displayed.

Figure 8:
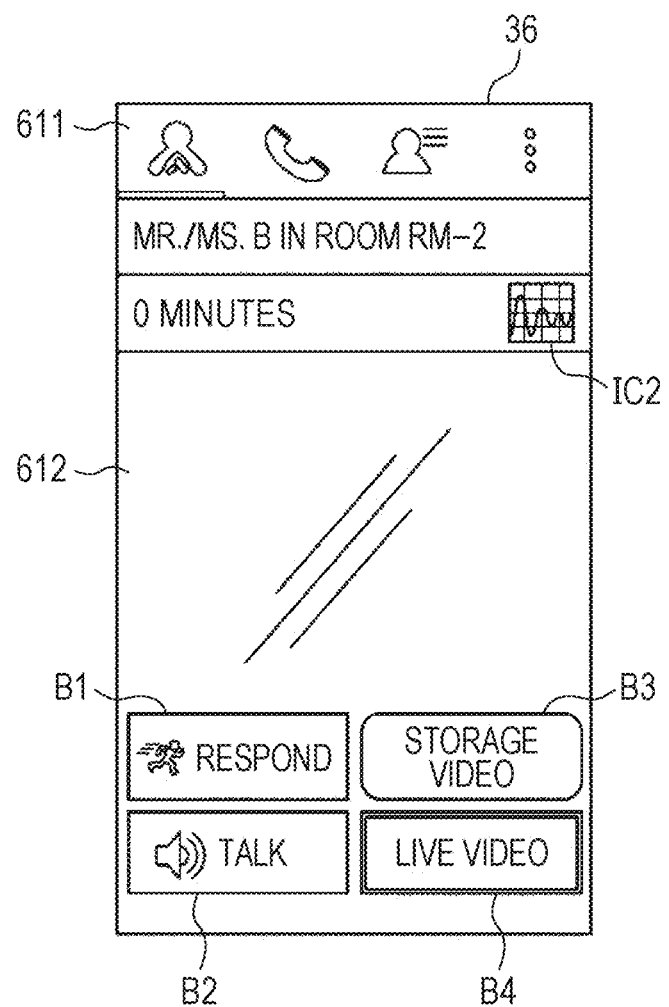
FIG. 8 is a diagram illustrating an example of a display screen of a mobile terminal according to a modified example.

FIG. 8 is a diagram illustrating another display screen example of the mobile terminal. In the example described above, the sensor box SB determines that the target person overturns or falls from the acquired image data and transmits the notification signal to the management server SV, but, for example, it is also possible to detect an abnormality in the subtle body movement and transmit the notification signal to the management server SV. In this case, similarly to the above example, the notification signal indicating the subtle body movement abnormality may be transmitted from the management server SV to the selected mobile terminal TA, and an icon IC2 indicating the subtle body movement abnormality may be displayed on the mobile terminal TA which has received the notification signal. In this case, the careworker can request image transfer (or transfer of subtle body movement data) for the living room by touching the button B3, and the careworker can talk directly with the target person through the SB sound input/output unit 12 of the sensor box SB by touching the button B2, and thus the careworker can accurately determine the situation. The analysis for the image captured by the camera and the state of the subtle body movement detected by the Doppler sensor may be combined and used for event determination.

Figure 9:
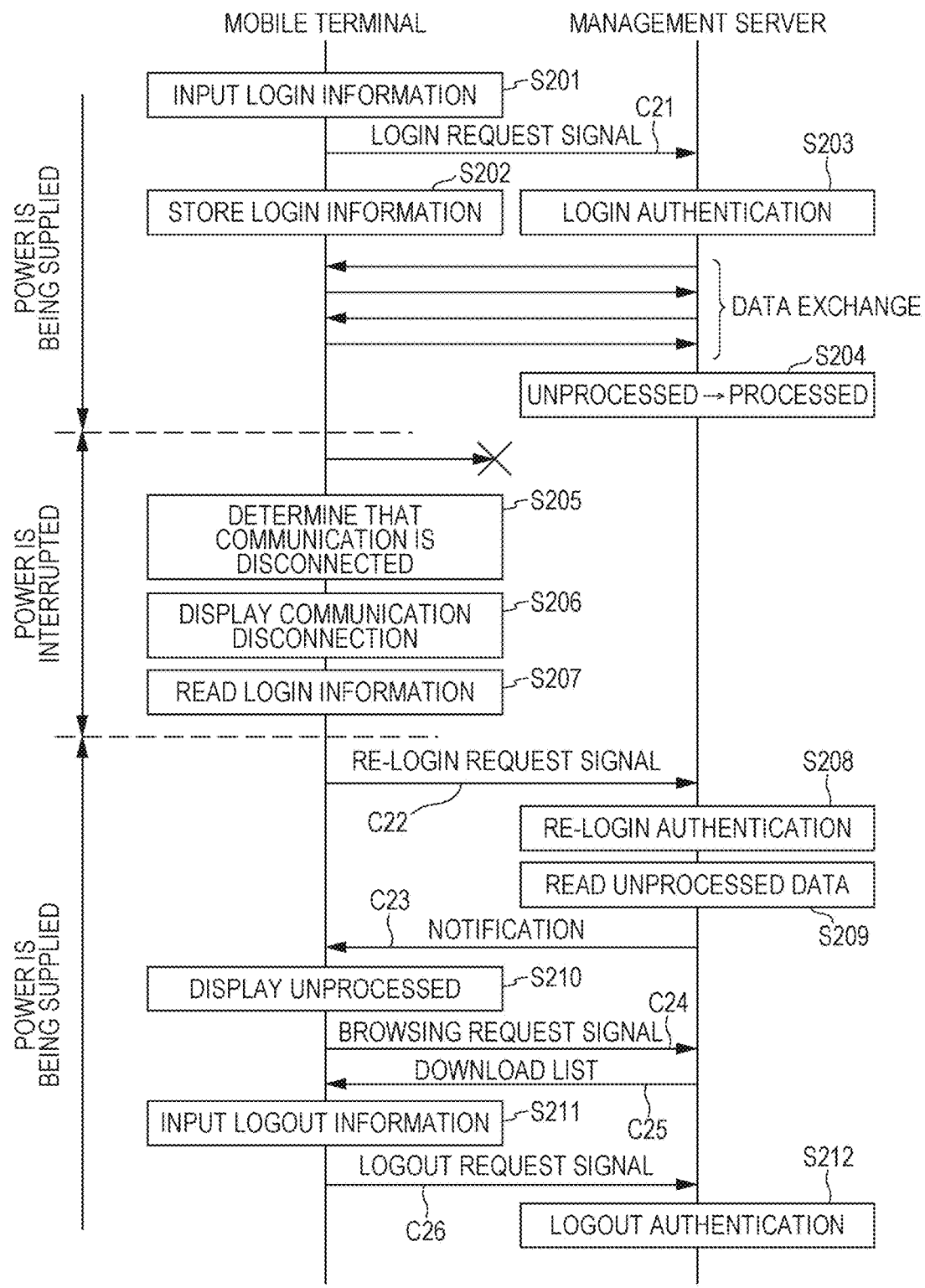
FIG. 9 is a ladder chart illustrating a communication process performed between a mobile terminal TA and a management server SV.
Figures 10, 11:
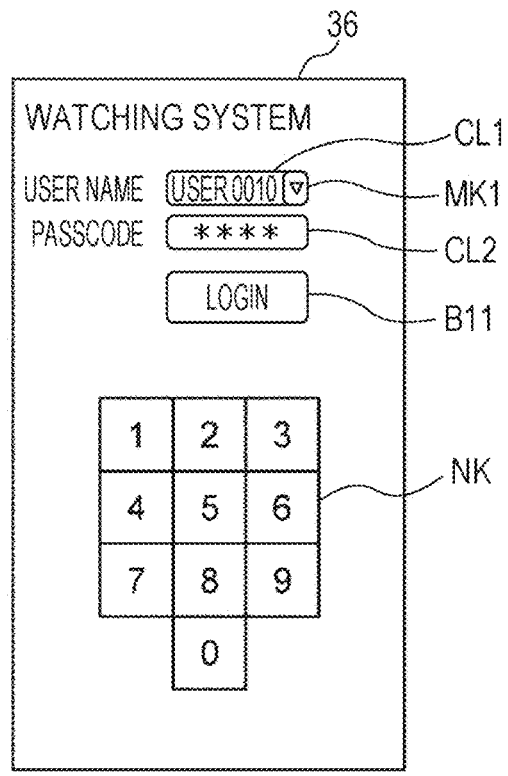
FIG. 10 illustrates a display example of a login screen of a mobile terminal.
FIG. 11 is a diagram illustrating a login list stored in an SV storage 22 of the management server SV

Next, a management server login process will be described. FIG. 9 is a ladder chart of a login process performed between the mobile terminal TA and the management server SV which is performed in parallel with the control of FIG. 6. Here, one of the careworkers who started work (user name: 0010) is assumed to perform a manipulation of turning on the main switch of the mobile terminal TA managed by him/herself. At this time, a login screen illustrated in FIG. 10 is displayed. In a mobile terminal using an OS such as "Android (registered trademark)," a standard login screen is displayed, but customization is performed so that the login screen illustrated in FIG. 10 is first displayed.

If a login manipulation is performed by the user in step S201 of FIG. 9, the mobile terminal which has logged in becomes valid as a part of the watching system. More specifically, if the user taps a triangular mark MK1 at a right end of a "user name" input field CL1 in the login screen illustrated in FIG. 10, a plurality of choices are displayed, and thus the user taps his/her own user name "0010" among the choices and selects the user name (user ID) and further inputs a four-digit number to a "passcode" input field CL2 using a number key NK displayed therebelow. Thereafter, the user taps a button B11 and completes the login manipulation. Here, the input of the passcode may be omitted.

With the login manipulation in step S201 in FIG. 3, a login request signal including a user name, a terminal ID (identifier information), or the like as information related to the user is transmitted from the mobile terminal (here, TA-7)

to the management server SV (C21). Further, in step S202, the mobile terminal TA-7 stores the user name or the terminal ID serving as login information used for logging-in the TA storage 32 (preferably, a non-volatile memory).

The management server SV which has received the login request signal from the mobile terminal TA-7 performs login authentication by checking whether or not the user name is identical to the passcode with reference to the inside of the database stored in the SV storage 22 (step S203), and if the user name is identical to the passcode, the management server SV executes the login process.

FIG. 11 is a diagram illustrating a login list stored in the SV storage 22 of the management server SV. The login list is a correspondence between the mobile terminal specified by the identifying information ID and the user who is currently in the log-in state using the mobile terminal. In the case of the mobile terminals (TA-4 and TA-6) which are not in use, the user name is blank. In the present embodiment, it is possible to use seven mobile terminals TA-1 to TA-7, and the user "0010" is added to the login list of FIG. 11 by logging in from the mobile terminal TA-7. The number of mobile terminals which can be used is arbitrary.

If the login authentication of the management server SV is completed, it is possible to access the mobile terminal TA-7 and the management server SV, and it is possible to view the notification destined for the mobile terminal TA-7. Alternatively, the management server SV permits downloading of necessary information (data transfer) in response to a request from the mobile terminal TA-7. Accordingly, the user "0010" can view information or the like of the target person Ob in charge of himself/herself and perform appropriate nursing care or the like. The management server SV generates a list of processed notifications and unprocessed notifications for each mobile terminal and stores the list in the database (step S204). Here, in a case in which the notification event information is received, the careworker in charge should respond as quickly as possible, but in the case of other normal notifications (for example, waking-up or the like of Mr./Ms. A and Mr./Ms. B), an agreement that it is preferable that any one of a plurality of careworkers in charge respond is reached. On the other hand, the normal notifications (content of a list LT1 to be described later) can be viewed by accessing the management server SV from the mobile terminal TA-7.

Figure 12A:
FIG. 12A illustrates an example of a list LT1 illustrating a notification in which a mobile terminal TA-7 carried by a user "0010" is a destination.

FIG. 12A illustrates an example of a list LT1 illustrating notifications destined for the mobile terminal TA-7 carried by the user "0010", and the list LT1 is stored in a hard disk of the management server SV or the like. Since the user "0010" is in charge of Mr./Ms. A and Mr./Ms. B as the watching target persons Ob, notifications from the other target persons are not performed. In a case in which the user "0010" accesses the list LT1 through the mobile terminal TA-7, and views the notification indicating that the sensor box detects waking-up of Mr./Ms. B (accesses the information on Mr./Ms. B) at, for example, at 9:38, if the user "0010" checks the state of Mr./Ms. B and then taps the corresponding button B1 in the screen display of FIG. 7B, the response signal is transmitted from the mobile terminal TA-7 to the management server SV (a response indicating responding [including what there is an intention to respond]) is transmitted), and the management server SV determines that the user "0010" has checked content of "Mr./Ms. B woke up" in the list LT1 accordingly, and changes a field of "check" to "checked". The information accessed and responded by the user as described above is referred to as processed information. The same applies to "Mr./Ms. A woke up" at 9:54. Here, the response signal may be transmitted to the management server SV in response to a manipulation on, for example, a switch of the sensor box SB (not illustrated) in addition to the manipulation of the user of tapping the corresponding button B1.

On the other hand, in a case in which there is a nurse call from Mr./Ms. A through the sensor box at 10:05, but the user "0010" does not check yet because the user is busy, the management server SV determines that the user "0010" does not checked content such as "nurse call from Mr./Ms. A" in the list LT1, and changes the field of "check" "not checked". The information which the user does not access yet or does not respond is referred to as unprocessed information. The same applies to "Mr./Ms. B leaving bed" at 11:22. Here, the processed information and the unprocessed information related to the target person Ob are not limited to the notification from the sensor box SB but include all pieces of information such as a dosing time of the target person Ob and nursing care content.

Here, it is assumed that a power outage occurs in the facility around 11:30, and the network NW shuts down. Since the mobile terminal TA-7 operates with the battery power, the mobile terminal TA-7 is not directly affected by the power outage, but the mobile terminal TA-7 (and other mobile terminals) and the management server SV are unable to communicate with each other. At this time, the mobile terminal TA-7 can no longer access the management server SV, in step S205 it is determined that communication with the management server SV is disconnected.

Figure 13:
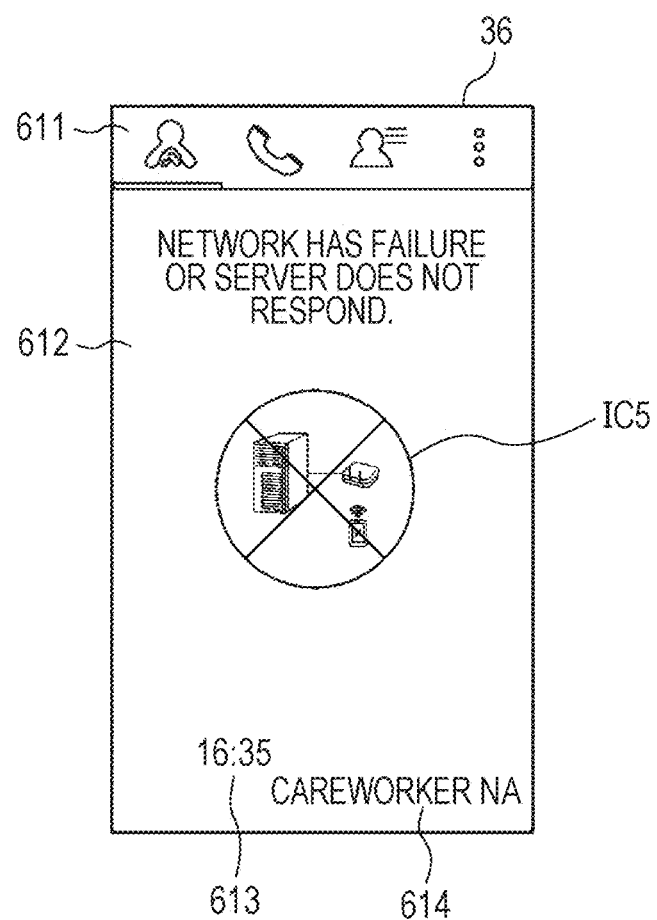
FIG. 13 illustrates an example of a screen displayed on a mobile terminal when the mobile terminal and the management server are unable to communicate with each other.

In this regard, as illustrated in FIG. 13, in step S206, the mobile terminal TA-7 displays a message "network has failure or server does not respond" in the main region 612 (information indicating that it is in a state in which communication with the management server is unable to be performed) information) together with the icon IC5 indicating a communication failure. The user "0010" who viewed it understands that communication with the management server SV is unable to be performed. At this time, the mobile terminal TA-7 rejects any input since it is in a state in which an input is unable to be performed while continuously displaying the screen illustrated in FIG. 13, and thus even in a case in which the mobile terminal TA-7 is brought out of the service area by a third party, the privacy of the target person is observed.

Alternatively, in step S207, the mobile terminal TA-7 reads the login information stored in the TA storage 32, generates a re-login request signal including the user name and the terminal ID, and automatically transmits the re-login request signal through the TA communication IF unit 33 (makes a reconnection request). In a case in which re-login authentication is performed using the login list (FIG. 11) generated on the management server SV side, the terminal ID has only to be included in the re-login list signal. Here, the mobile terminal TA-7 may return to the login screen (FIG. 10), the user may manually perform the login input manipulation again, and this becomes a reconnection request as well.

However, as long as the network NW shuts down, the re-login request signal is not received by the management server SV, and no response signal is transmitted. In this regard, the mobile terminal TA-7 keeps repeatedly transmitting the re-login request signal for a predetermined period (for example, 30 minutes). Further, in a case in which a predetermined period of time elapses, the screen display of the mobile terminal TA-7 can be returned to the login screen illustrated in FIG. 10.

On the other hand, while the network NW shuts down, power supply to the management server SV is often interrupted, but data (including the list LT1 including the unprocessed information and the processed information) in a hard disk is stored. Further, if the sensor box SB is of a type that operates with a battery or the like, while the network NW shuts down, data collected from the target person Ob can be stored in the SB storage 16 and transmitted to the management server SV after the network NW is recovered.

Here, it is assumed that the power outage is recovered around 12 o'clock, and the network NW starts to operate normally. In a case in which the recovery is completed within a predetermined period, the management server SV receives the re-login request signal from the mobile terminal TA-7(C22).

In response to the re-login request signal, in step S208, the management server SV performs the login authentication again (resumes or continues logging-in) on the basis of the user name and the terminal ID included in the re-login request signal. If the login list (FIG. 11) is used, it is possible to perform the login authentication (resume or continue logging-in) again on the basis of only the terminal ID. Then, in step S209, the management server SV reads the list LT1 from the stored database. Here, immediately before the network NW shuts down, two notifications preceding in time among four notifications in the list LT1 has been checked by the user "0010". In this regard, the management server SV counts notifications which are not checked by the user "0010" from the list LT1, and transmits it to the mobile terminal TA-7 as information indicating that the unprocessed information is stored (C23). This is performed for each mobile terminal.

Figure 12B:
FIG. 12B illustrates an example of a list LT2 illustrating only an unprocessed notification.
Figure 14:
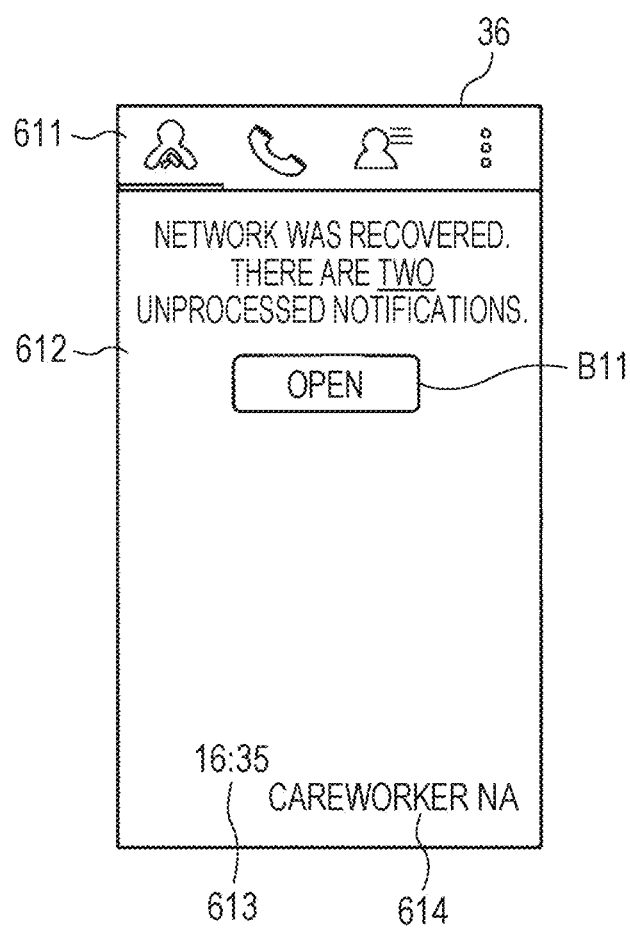
FIG. 14 illustrates an example of a screen displayed on the mobile terminal when communication between the mobile terminal and the management server is recovered.

In step S210, as illustrated in FIG. 14, the mobile terminal TA-7 which has received this information displays a message "network was recovered. There are two unprocessed notifications" (the information indicating that the unprocessed information is stored) in the main region 612 together with an "open" button B12 (making it possible to access unprocessed information). Here, the presence of an unprocessed notification may be presented via a sound, vibration, or the like without displaying it on the mobile terminal TA-7. Here, if the user "0010" taps the "open" button B12, a browsing request signal is transmitted from the mobile terminal TA-7 to the management server SV (C24). In response to the browsing request signal, the management server SV causes the mobile terminal TA-7 to download a list LT2 of the unprocessed information illustrated in FIG. 12B (C25). Here, as long as the unprocessed information and the processed information are clearly distinguished like the list LT1, the list LT1 in which both pieces of information are mixed may be downloaded to the mobile terminal TA-7. Further, if the unprocessed information is not stored at a time point at which communication is interrupted, the management server SV does not transmit information to the mobile terminal TA-7 or transmits information indicating that the number of unprocessed information is 0. In this case, the "open" button B12 is not displayed.

The user "0010" can check content that the user should respond while viewing the list LT2 displayed on the display screen of the mobile terminal TA-7. In a case in which the user "0010" taps the corresponding button B1 (FIG. 7B) for each notification, the "check" field of the corresponding content of the list LT1 stored in the management server SV becomes "checked".

In a case in which the user "0010" finishes employment, logout information is input by manipulating a logout button (not illustrated) displayed on the mobile terminal TA-7 (step S211). Then, a logout request signal including the user name and the terminal ID serving as the logout information is transmitted from the mobile terminal TA-7 to the management server SV (C26). Upon receiving the logout request signal, in step S212, the management server SV executes a logout process. Specifically, the management server SV deletes the user name corresponding to the mobile terminal TA-7 in the login list of FIG. 11 and leaves it blank, and transmission of information and the like from the management server SV to the mobile terminal TA-7 are not performed at all until the user logs in next.

The present invention is not limited to the embodiment described in the specification but it is obvious to those skilled in the art from the embodiment or the technical spirit described in this specification that other embodiments and modifications are included in the present invention. The description and the embodiment of the specification are merely for the purpose of illustration only, and the scope of the present invention is indicated by claims set forth below. For example, in the above-described embodiment, the example in which the mobile terminal is unable to perform communication with the management server while it goes out of the service area has been described, but the embodiment can be applied, for example, even in a case in which a failure occurs in the management server, and thus communication is unable to be performed in addition to the power outage. In this case, it is possible to detect that the management server shuts down through another monitoring device and perform the above-described control. Alternatively, similar control can be performed even in a case in which the mobile terminal moves outside the network away from the access point and then returns. Further, in the above-described embodiment, executing logging-in again by transmitting the re-login request signal from the mobile terminal after the communication between the mobile terminal and the management server is recovered becomes a condition that the notification of the unprocessed information is performed from the management server, but the notification of the unprocessed information may be performed from the management server immediately at a time point at which the communication between the mobile terminal and the management server is recovered.

REFERENCE SIGNS LIST

11 SENSOR UNIT
12 SB SOUND INPUT/OUTPUT UNIT
13 NURSE CALL INPUT UNIT
14 SB CONTROL PROCESSING UNIT
15 SB COMMUNICATION IF UNIT
16 SB STORAGE
21 SV CONTROL PROCESSING UNIT
22 SV STORAGE
23 SV COMMUNICATION IF UNIT
24 SV INPUT UNIT
31 SV CONTROL PROCESSING UNIT
32 SV STORAGE
33 SV IF UNIT
34 TA SOUND INPUT/OUTPUT UNIT
35 TA INPUT UNIT
36 TA DISPLAY UNIT
37 TA IF UNIT
41 NOTIFICATION DESTINATION INFORMATION TABLE
111 DOPPLER SENSOR
112 CAMERA
141 SB CONTROL UNIT
142 BEHAVIOR DETECTION PROCESSING UNIT
143 NOTIFICATION PROCESSING UNIT

144 STREAMING PROCESSING UNIT
145 NURSE CALL PROCESSING UNIT
211 SV CONTROL UNIT
221 NOTIFICATION DESTINATION INFORMATION STORAGE
311 TA CONTROL UNIT
312 TA PROCESSING UNIT
321 DISPLAY SCREEN STORAGE
411 NOTIFICATION SOURCE ADDRESS FIELD
412 NOTIFICATION EVENT FIELD
413 NOTIFICATION DESTINATION ADDRESS FIELD
611 MENU BAR REGION
612 MAIN REGION
3121 DISPLAY PROCESSING UNIT
AP ACCESS POINT
IC1 to IC5 ICON
MS WATCHING SYSTEM
NW NETWORK
Ob TARGET PERSON
RM LIVING ROOM
SB SENSOR BOX
SP FIXED TERMINAL DEVICE
ST NURSE STATION
SV MANAGEMENT SERVER
TA MOBILE TERMINAL

The invention claimed is:

1. A watching system comprising:
a sensor device that receives data from a watching target person and outputs a signal corresponding to the data;
a management server that is communicably connected to the sensor device via a network; and
a mobile terminal that is capable of performing wireless communication with the management server via the network and outputs a watching alarm on the basis of a signal transmitted from the sensor device via the management server,
wherein, when the mobile terminal transmits login information to the management server via the network, the management server permits the mobile terminal to log in, so that information related to the watching target person stored in the management server is accessible from the mobile terminal, and the management server causes transition from unprocessed information to processed information to be performed in a case in which there is a response indicating responding in the information related to the watching target person accessed from the mobile terminal,
when the mobile terminal transmits logout information to the management server, the management server permits the mobile terminal to log out, so that the information related to the watching target person stored in the management server is inaccessible from the mobile terminal, and
in a case in which the mobile terminal that has logged in is unable to perform communication with the management server, the management server stores the unprocessed information before the communication is unable to be performed, and then when the mobile terminal is able to perform communication with the management server, the management server transmits a notification indicating that the unprocessed information is stored to the mobile terminal, and the mobile terminal presents information indicating that the unprocessed information is stored to the management server in response to the notification.

2. The watching system according to claim 1, wherein, in a case in which the mobile terminal that has logged in is unable to perform communication with the management server, and then the mobile terminal is able to perform communication with the management server, when a reconnection request is made from the mobile terminal, the management server resumes or continues logging-in by the mobile terminal.

3. The watching system according to claim 2, wherein, in a case in which the login information is stored, and the mobile terminal that has logged in is unable to perform communication with the management server, the mobile terminal makes the reconnection request by repeatedly transmitting the login information to the management server automatically, and prohibits a user from inputting.

4. The watching system according to claim 2, wherein the mobile terminal includes a touch panel type screen that displays the information indicating that the unprocessed information is stored to the management server and a button that is manipulated by a user and causes the unprocessed information stored in the management server to be accessible in accordance with the notification indicating that the unprocessed information is stored which is transmitted from the management server in a case in which the logging-in is resumed or continued.

5. The watching system according to claim 2, wherein, in a case in which the mobile terminal is unable to perform communication with the management server, if a predetermined period elapses, the mobile terminal returns to a state in which an input of the login information is received.

6. The watching system according to claim 3, wherein the mobile terminal includes a touch panel type screen that displays the information indicating that the unprocessed information is stored to the management server and a button that is manipulated by a user and causes the unprocessed information stored in the management server to be accessible in accordance with the notification indicating that the unprocessed information is stored which is transmitted from the management server in a case in which the logging-in is resumed or continued.

7. The watching system according to claim 3, wherein, in a case in which the mobile terminal is unable to perform communication with the management server, if a predetermined period elapses, the mobile terminal returns to a state in which an input of the login information is received.

8. The watching system according to claim 4, wherein, in a case in which the mobile terminal is unable to perform communication with the management server, if a predetermined period elapses, the mobile terminal returns to a state in which an input of the login information is received.

9. The watching system according to claim 1, wherein, in a case in which the mobile terminal is unable to perform communication with the management server, if a predetermined period elapses, the mobile terminal returns to a state in which an input of the login information is received.

10. A management server comprising:
a communication unit that performs communication with a sensor device that receives data from a watching target person and outputs a signal corresponding to the data, and a mobile terminal that outputs a watching alarm on the basis of a signal transmitted from the sensor device, via a network; and
a storage that stores various kinds of information,
wherein, when login information transmitted by the mobile terminal via the network is received by the communication unit, the mobile terminal is permitted to log in, so that information related to the watching target person stored in the storage is accessible from the mobile terminal, transition from unprocessed information to processed information is performed in a case in which there is a response indicating responding in the information related to the watching target person accessed from the mobile terminal, when logout information transmitted from the mobile terminal is received by the communication unit, the mobile terminal is permitted to log out, so that the information related to the watching target person stored in the storage is inaccessible from the mobile terminal, and in a case in which the mobile terminal that has logged in is unable to perform communication with the management server, the unprocessed information before the communication is unable to be performed is stored in the storage, and then when the mobile terminal is able to perform communication with the management server, a notification indicating that the unprocessed information is stored in the storage is transmitted from the communication unit to the mobile terminal, and the mobile terminal is able to present information indicating that the unprocessed information is stored in the storage in response to the notification.

* * * * *